US006271352B1

(12) United States Patent
Nielsen et al.

(10) Patent No.: US 6,271,352 B1
(45) Date of Patent: Aug. 7, 2001

(54) PAI-1 DETERMINATION AND USE THEREOF

(75) Inventors: Lars S. Nielsen, Kokkedal; Peter Andreasen, Dragor; Keld Dano, Charlottenlund; Nils Brunner, Virum, all of (DK)

(73) Assignee: Fonden til Fremme af Eksperimentel Cancerforskning, Copenhagen (DK)

( * ) Notice: Subject to any disclaimer, the term of this patent is extended or adjusted under 35 U.S.C. 154(b) by 0 days.

(21) Appl. No.: 08/466,965

(22) Filed: Jun. 6, 1995

Related U.S. Application Data

(63) Continuation-in-part of application No. 07/900,364, filed on Jun. 18, 1992, now Pat. No. 5,422,245, which is a continuation of application No. 07/752,990, filed on Sep. 3, 1991, now abandoned, which is a continuation of application No. 07/035,995, filed on Mar. 11, 1987, now abandoned.

(30) Foreign Application Priority Data

Jul. 12, 1985 (DE) ...................................... 3196/85

(51) Int. Cl.[7] .............................. C07K 1/00; C12N 5/12
(52) U.S. Cl. ..................... 530/387.1; 530/388.1; 530/388.2; 530/388.24; 530/388.8; 935/93; 935/106; 935/108; 435/326
(58) Field of Search ................. 435/7.1, 326; 530/388.1, 530/387.1, 388.2, 388.24, 388.8; 424/130.1, 138.1; 935/93, 106, 108

(56) References Cited

U.S. PATENT DOCUMENTS

| 4,952,512 | 8/1990 | Loskutoff et al. . |
| 5,314,994 | 5/1994 | Loskutoff et al. . |
| 5,629,160 | 5/1997 | Loskutoff et al. . |

FOREIGN PATENT DOCUMENTS

| 0187814 | 7/1986 | (EP) . |
| 0277212 | 4/1995 | (EP) . |

OTHER PUBLICATIONS

Tockman et al (Cancer Res., 52:2711s–2718s), 1992.*
Unbehaun et a (Anticancer Res, 15:2407 #6Q), 1995.*
Taber's Cyclopedic Medical Dictionary, 16th Ed, F.A. Davis Co, Philadelphia, p. 42, 1989.*
Pierga et al (Br. J. Cancer, 7 6:537–540), 1997.*
Campbell (Monoclonal Antibody Technology, Elsevier Press pp. 1–32), 1984.*
Coleman et al (JBC, 257:4260–4264), 1982.*
Andreasen, et al., Plasminogen activator inhibitor type–1: reactive center and amino–terminal heterogeneity determined by protein and cDNA sequencing, FEBS, vol. 209, No. 2, pp. 213–218, Dec. 1986.
Andreasen, et al., Plasminogen activator inhibitors: hormonally regulated serpins, Molecular and Cellular Endocrinology, vol. 68, pp. 1–19, 1990.

Declerck, et al., Measurement of Plasminogen Activator Inhibitor 1 in Biologic Fluids With a Murine Monoclonal Antibody–Based Enzyme–Linked Immunosorbent Assay, Blood, vol. 71, No. 1, pp. 220–225, 1988.

De Witte, et al., Complexes Between Urokinase–Type Plasminogen Activator and its Receptor in Blood as Determined by Enzyme–Linked Immunosorbent Assay, Int. J. Cancer, vol. 77, pp. 236–242, 1998.

Ginsburg, et al., cDNA Cloning of Human Plasminogen Activator–Inhibitor from Endothelial Cells, J. Clin. Invest., vol. 78, pp. 1673–1680, Dec. 1986.

Grondahl–Hansen, et al., Sensitive and specific enzyme–linked immunosorbent assay for urokinase–type plasminogen activator and its application to plasma from patients with breast cancer, J. Lab. Clin. Med., vol. 111, No. 1, pp. 42–51, 1988.

Heckman, et al., Endothelial Cells Produce a Latent Inhibitor of Plasminogen Activators That Can be Activated by Denaturants, Journal of Biological Chemistry, vol. 260, No. 21, pp. 11581–11587, 1985.

Kato, et al., Immunoassay of three enolase isozymes in human serum and in blood cells, Clinica Chimica. Acta., vol. 127, pp. 353–363, 1983.

Kawano, et al., Urokinase Inhibitor in Human Placenta, Nature, vol. 217, pp. 253–254, 1968.

Kawano, et al., Partial Purification and Properties of Urokinase Inhibitor from Human Placenta, The Journal of Biochemistry, vol. 67, No. 3, 1970.

Kruithof, et al., Plasminogen Activator Inhibitor 1: Development of a Radioimmunoassay and Observations on Its Plasma Concentration During Venous Occlusion and After Platelet Aggregation, Blood, vol. 70, No. 5, pp. 1645–1653, 1987.

Lecander, et al., Differential inhibition of two molecular forms of melanoma cell plasminogen activator by a placental inhibitor, British Journal of Haematology, vol. 57, pp. 407–412, 1984.

Lindahl, et al., Purification of high and low molecular weight plasminogen activator inhibitor 1 from fibrosarcoma cell: line Ht 1080 conditioned medium, Biochimica Et Biophysica Acta., vol. 994, pp. 253–257, 1989.

(List continued on next page.)

Primary Examiner—Susan Ungar
(74) Attorney, Agent, or Firm—Iver P. Cooper

(57) ABSTRACT a monoclonal antibody which binds a human endothelial type plasminogen activator inhibitor (PAI-1) produced by dexamethasone-treated human HT-1080 fibrosarcoma cells may be used, inter alia, for determining PAI-1 protein abundance in tumor tissue or a sample of a body fluid. Measurements of this parameter may be useful in predicting the presence or metastasis of a tumor, or of predicting the progression of a known malignant tumor.

21 Claims, 12 Drawing Sheets

OTHER PUBLICATIONS

Nielsen, et al., Plasminogen Activator Inhibitors from Placenta and Fibrosarcoma Cells Are Antigenically Different As Evaluated With Monoclonal and Polyclonal Antibodies, Thrombosis Research, vol. 46, pp. 411–423, 1987.

Nielsen, et al., Plasminogen activators catalyses conversion of inhibitor from fibrosarcoma cells to an inactive form with a lower apparent molecular mass, FEBS, vol. 196, No. 2, pp. 269–273, 1986.

Pedersen, et al., The complex between urokinase plasminogen activator and its type–1 inhibitor in breast cancer extracts quantitated by ELISA, Journal of Immunological Methods, vol. 203, pp. 55–65, 1997.

Rijken, et al., Purification and Characterization of the Plasminogen Activator Secreted by Human Melanoma Cells in Culture, Journal of Biological Chemistry, vol. 256, No. 13, pp. 7035–7041, 1981.

Sprenger, et al., Evidence For The Presence of Two Different Fibrinolytic Inhibitors In Human Endothelial Cell Conditioned Medium, Biochimica Et Biophysica Acta., vol. 801, pp. 163–170, 1984.

Tanaka, et al., Plasminogen Activator Inhibitor 1 in Human Carcinoma Tissues, Int. J. Cancer, vol. 48, pp. 481–484, 1991.

Wagner, et al., Purification of an Active Plasminogen Activator Inhibitor Immunologically Related to the Endothelial Type Plasminogen Activator Inhibitor from the Conditioned Media of a Human Melanoma Cell Line, Journal of Biological Chemistry, vol. 261, No. 31, pp. 14474–14481, 1986.

Andreasen, et al., Inactive proenzyme to tissue–type plasminogen activator from human melanoma cells, identified after affinity purification with a monoclonal antibody, The EMBO Journal, vol. 3, No. 1, pp. 51–56, 1984.

Dano, et al., Plasminogen Activating Enzyme in Cultured Glioblastoma Cells, Journal of Histochemistry and Cytochemistry, vol. 30, No. 11, pp. 1165–1170, 1982.

Hamer, et al., A Novel Protease Complex Assay for the Determination of Active Proteolysis in Cancer Patients, Oncogene Science, Abstract, 1998.

Kaltoft, et al., Monoclonal antibody that specifically inhibits a human M 52,000 plasminogen–activating enzyme, Proc. Natl. Acad. Sci. USA, vol. 79, pp. 3720–3723, Jun. 1982.

Nielsen, et al., Purification of Zymogen to Plasminogen activator from Human Glioblastoma Cells by Affinity Chromatography with Monoclonal Antibody, Biochemistry, vol. 21, pp. 6410–6415, 1982.

Nielsen, et al., Monoclonal antibody to human 66 000 molecular weight plasminogen activator from melanom cells. Specific enzyme inhibition and one–step affinity purification, EMBO Journal, vol. 2, No. 1, pp. 115–119, 1983.

Watanabe, Takeshi, Cell Technology, vol. 1, No. 1, pp. 23–30, 1982.

Schattauer Verlag, F.K., "Journal of the International Society on Thrombosis and Haemostasis," 54(1):269, abstracts No. P1594 and P1597 (1985).

Goding, J.W., "Monoclonal Antibodies; Principles and Pratices. Production and Application of Monoclonal Antibodies in Cell Biology, Biochemistry and Immunology," Academic Press, Inc., pp. 56–63 (1983).

Katz, D.H., "Monoclonal Antibodies and T Cell Products," CRC Press, Inc. pp. 1–7 (1982).

Secher, et al., "A Monoclonal Antibody for Large–Scale Purification of Human Leukocyte Interferon," *Nature* 285: 446–450 (1980).

Erickson, L.A., et al., "Reverse Fibrin Autography: A Method to Detect and Partially Characterize Protease Inhibitors after Sodium Dodecyl Sulfate–Polycrylamide Gel Electrophoresis," *Analytical Biochemistry* 137:454–463 (1984).

Schleef, et al., "A Quantitative, Functional Assay for Inhibitors of Tissue–Type Plasminogen Activator," *Circulation* 70, supp II, abstract 1467 (1984).

Holmsen, et al., "The Selectivity of the Thrombin–induced Platelet Release Reaction: Subcellular Localization of Released and Retained Constituents," *J. Lab. Clin. Med.* 75(5):840–855 (1970).

Paul, D., et al., "Human Platelet Basic Protein Associated with Antiheparin and Mitogenic Activities: Purification and Partial Characterization," *Proc. Natl. Acad. Sci. USA* 77(10):5914–5918 (1980).

Gogstad, G.O., et al., "Evidence for Release of Soluble, but not of Membrane–Integrated, Proteins from Human Platelet α–Granules," *Biochimica et Biophysica Acta* 702:81–89 (1982).

Watanabe, "Monoclonal Antibodies," *Cell Technology* 1(1):23–38 (1982).

Rebois, R.V., et al., "Antibodies Against Human Chorionic Gonadotropin Convert the Deglycosylated Hormone from an Antagonist to an Agonist," *The Journal of Biological Chemistry* 259(13):8087.

Richardson, M.C., et al., "Inhibitory Action of Chemically Deglycosylated Human Chorionic Gonadotrophin on Hormone–Induced Steroid Production by Dispersed Cells from Human Corpus Luteum," *Journal of Endocrinology* 101:327–332 (1984).

Sairam, M.R., et al., "Studies on Pituitary Follitropin XII. Enchanced Thermal Stability Induced by Chemical Deglycosylation," *Molecular and Cellular Endocrinology* 28:151–159 (1982).

Sairam, M.R., et al., "Studies on Pituitary Follitropin XI. Induction of Hormonal Antagonistic Activity by Chemical Deglycosylation," *Molecular and Cellular Endocrinology* 28:139–150 (1982).

Wohlwend, A., et al., "Plasminogen Activator–Specific Inhibitors Produced by Human Monocytes/Macrophages," *J. Exp. Med.* 165:320–359 (1987).

* cited by examiner

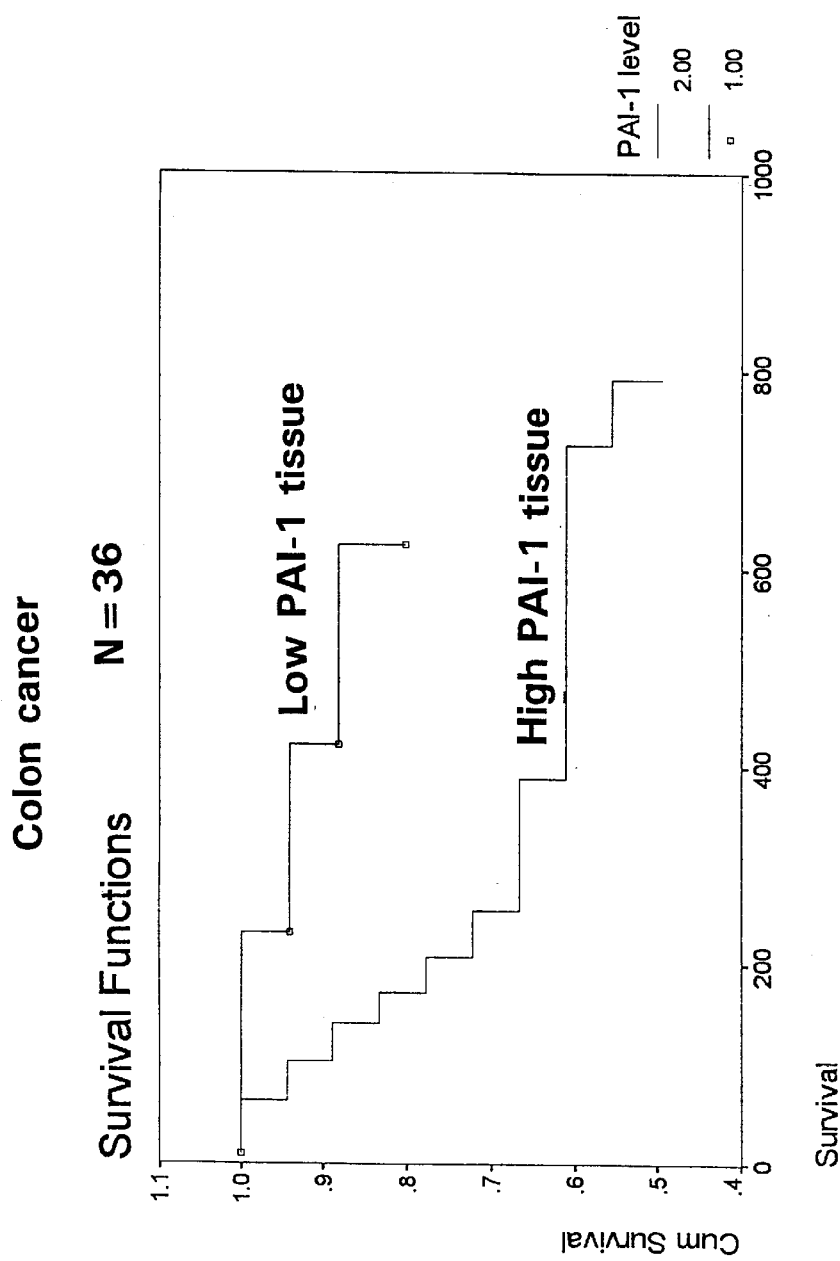

PAI-1 DETERMINATION AND USE THEREOF

The present invention is a continuation-in-part application of application No. 07/900,364 filed Jun. 18, 1992 now U.S. Pat. No. 5,422,245, which is a Rule 1.62 continuation application of No. 07/752,990 filed Sep. 3, 1991 now abandoned, which is a Rule 1.62 continuation application of No. 07/035,995 filed Mar. 11, 1987 now abandoned.

TECHNICAL FIELD

This invention relates to monoclonal antibodies, a method of producing such antibodies, hybridoma cells capable of producing the antibodies and uses of the antibodies. Furthermore, the invention relates to the prognostic and diagnostic use of PAI-1 determinations in e.g. plasma samples, and to measurement of uPA:PAI-1 complexes and uses thereof.

BACKGROUND ART

The fusion of mouse myeloma cells with spleen cells from immunized mice (Köhler and Milstein, Nature (1975), 256, 496–497) was the first indication that it is possible to obtain continuous cell lines which produce homogenous (so-called "monoclonal") antibodies. Since then, a large number of attempts have been made to produce various hybrid cells (so-called "hybridomas") antibodies. Since then, a large number of attempts have been made to produce various hybrid cells (so-called "hybridomas") and to employ the antibodies formed by these cells for various scientific investigations (cf. Current Topics in Microbiology and Immunology, volume 81—"Lymphocye Hybridomas", F. Melchers et. al., Springer-Verlag (1978) and references therein; C. J. Barnstable et al., Cell, (1978), 14, 9–20; P. Parham, W. F. Bodmer, Nature (1978), 276, 397–399; Handbook of Experimental Immunology, 3rd edition, vol. 2, D. M. Wier, editor, Blackwell, 1978, Chapter 25, Chem. Eng. News, 15–17 (1979); Kennett, R. H., McKearn, J. T., and Bechtol, K. B. (1980) Monoclonal Antibodies. Aybridomas: A New Dimension in Biological Analysis (Plenum, N.Y.)). These reports describe the principal techniques for the production of monoclonal antibodies by hybridomas.

Monoclonal antibodies against human plasminogen activators (urokinase-type (u-PA) and tissue-type (t-PA)) and produced by hybridomas have been prepared and have been used for purification, identification, and immunochemical localization of the activators and their proenzymes (Kaltoft, K., Nielsen, L. S., Zeuthen, J., and Danø, K. (1982) Proc. Natl. Acad. Sci. USA, 79, 3720–3723; Nielsen, L. S., Hansen, J. G., Andreasen, P. A., Skriver, L., Danø, K., and Zeuthen, J. (1983) The EMBO Journal, 2, 115–119; Nielsen, L. S., Hansen, J. G., Skriver, L., Wilson, E. L., Kaltoft, K., Zeuthen, J., and Danø, K. (1982), J. Histochem. Cytochem., 30, 1165–1170). Andreasen, P. A., Nielsen, L. S., Grøndahl-Hansen, J., Skriver, L., Zeuthen, J., Stephens, R. W., and Danø, K. (1984), The EMBO Journal, 3, 51–56). It has recently been shown that inhibitors of plasminogenn activators play an important role in the regulation of the plasmin mediated proteolysis. Such inhibitors have been identified in a variety of tissues, body fluids and cultured cell lines (Holmberg, L, Lecander, I., Persson, B., and Åstedt, B. (1978), Biochim. Biophys. Acta, 544 128–137; Seifert, S. C. and Gelehrter, T. D. (1978) Proc. Natl. Acad. Sci. USA, 75, 6130–6133; Chmielewska, J., Ranby, M., and Wiman, B. (1983) Thromb. Res., 31, 427–431; Emeis, J. J., Van Hindsbergh, V. W. M., Verheijen, J. H. and Wijngaards, G. (1983) Biochem. Biophys. Res. Commun., 110, 391–398; Golder, J. P. and Stephens, R. W. (1983) Eur. J. Biochem., 136, 517–522; Loskutoff, D. J., van Mourik, J. A., Erickson, L. A., and Lawrence, D. (1983). Proc. Natl. Acad. Sci. USA, 80, 2956–2960; Philips, M., Juul, A. G., and Thorsen, S. (1984)Biochim. Biophys. Acta, 802, 99–110; Vassalli, J. D., Dayer, J. M., Wohlwend, A. and Belin, D. (1984) J. Exp. Med., 159, 1653–1668; Erickson, L. A., Ginsberg, M. H., and Loskutoff, D. J., (1984), J. Clin. Invest., 74, 1465–1472; Cwikel, B. J., Barouski-Miller, P. A., Coleman, P. L., and Gelehrter, T. D. (1984), J. Biol. Chem., 259, 6847–6851; Åstedt, B., Lecanders, I., Brodin, T., Lundblad, A., and Löw, K. (1985), Thrombos.Haemost, 53, 122–125; J. Biol Chem. (1985), 260, 7029–7034).

The mutual relationship of these inhibitors is at present not fully clarified, although recent evidence indicates that at least three immunologically dissimilar types of plasminogen activator inhibitors exist. These include (1) protease nexin, (2) plasminogen activator inhibitor purified from placenta (Åstedt, B., Lecander, I., Brodin, T., Lundblad, A., and Löw, K., (1985) Thromb. Haemost. 53, 122–125), and (3) plasminogen activator inhibitors that inhibit u-PA and t-PA and which typically have been obtained from human endothelial cells, human blood platelets, and rat hepatoma cells (HTC), in the following referred to as endothelial type plasminogen activator inhibitor (e-PAI).

An inhibitor with remarkable similarities to e-PAI has been found in human plasma (Thorsen, S. and Philips, M. (1984) Biochim. Biophys. Acta 802, 111–118).

Monoclonal antibodies against placental plasminogen activator inhibitor have been prepared and such antibodies have been used for the purification of said inhibitor (Åstedt, B., Lecander, I., Brodin, T., Lundblad, A., and Löw, K., (1985) Thromb. Haemost. 53, 122–125).

SUMMARY OF THE INVENTION

The present invention provides monoclonal antibodies against the endothelial type plasminogen activator inhibitor and immunologically similar inhibitors.

The term "immunologically similar inhibitors" denotes plasminogen activator inhibitors which cross-react with polyclonal or monoclonal antibodies raised against inhibitors derived from any of the sources mentioned in connection with the above definition of endothelial type plasminogen activator inhibitor.

The provision of these antibodies makes it possible to study the role of plasminogen activator inhibitors in plasmin mediated proteolysis including fibrinolysis and the mutual relationship of the above mentioned plasminogen activator inhibitors. Moreover, such monoclonal antibodies are useful for the purification of plasminogen activator inhibitor by means of immunoadsorption chromatography, for removal of the inhibitor from body fluids and other biological materials by means of immunoadsorption, for neutralization of the inhibitory activity of the plasminogen activator inhibitor and for the detection, identification and quantification, e.g. by the ELISA technique, of plasminogen activator inhibitor in body fluids, normal or malignant cells and tissues, and other biological materials.

The invention also provides a method of producing the above mentioned antibodies. This method comprises fusing myeloma cells with antibody-producing cells obtained from mammals which have been immunized with endothelial type plasminogen activator inhibitor or immunologically similar inhibitors or with antibody-producing cells which in vitro has been immunized with said plasminogen activator inhibitor, and selecting the hybridomas producing antibodies against the above mentioned inhibitors. Thus the hybridomas are produced by a derivation of the method of Köhler and Milstein mentioned above. The antibody-producing cells used are preferably spleen cells or lymph node cells. The particular species of mammals from which the myeloma and antibody producing cells are derived is not critical insofar as it is possible to fuse the cells of the one species with another, e.g. mouse to rat, rat to human, or mouse to human.

It is preferred, however, to use the same species of animal as a source of both myeloma and anti plasminogen activator inhibitor antibody-producing cells. One preferred cell line for the practice of this invention is a fused cell hybrid between a plasminogen activator inhibitor primed mouse spleen cell and a mouse myeloma cell.

The hybridomas resulting from the fusion are systematically examined for production of antibodies which selectively react with plasminogen activator inhibitor.

It should be noted that monoclonal antibodies raised against a single antigen may be distinct from each other depending on the determinant that induced their formation; but for any given hybridoma (clone), all of the antibodies it produces are monospecific for a particular antigenic determinant in the plasminogen activator inhibitor molecule.

The invention also relates to hybridoma cells capable of producing monoclonal antibodies against the endothelial type plasminogen activator inhibitor and immunologically similar inhibitors.

BRIEF DESCRIPTION OF THE DRAWINGS

The invention will now be described in more detail with reference to the drawings in which FIG. 6 is a univariate analysis of tumour PAI-1 content in 57 patients with colon adenocarcinoma.

DETAILED DESCRIPTION OF THE PREFERRED EMBODIMENTS OF THE INVENTION

Figure 1:
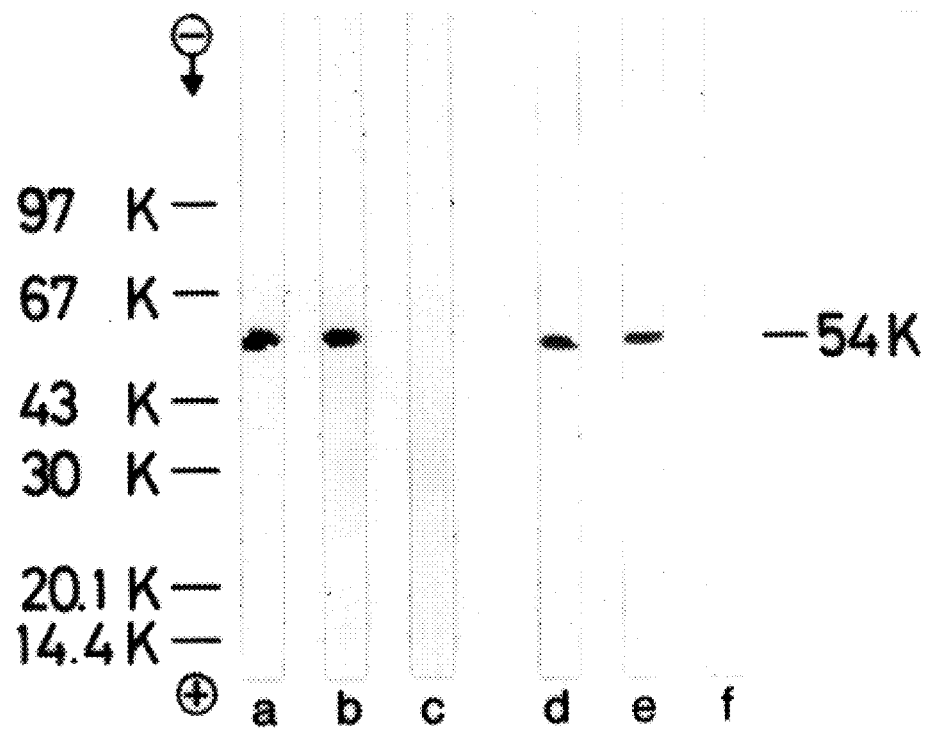
FIG. 1 is a zyogram showing reverse zymography for plasminogen activator inhibitor in culture fluid conditioned by dexamethasone-treated human fibrosarcoma cells of the line HT-1080 or umbilical cord endothelial cells before and after passage through Sepharose columns coupled with monoclonal antibodies against trinitrophenyl (control) and e-PAI.

In general, the production of the hybridomas comprises the following steps:

A. Immunization of mammals with partially purified plasminogen activator inhibitor. Balb/c-mice have been found useful for this purpose, but other mammals can also be used. The immunization scheme and the concentration of plasminogen activator inhibitor should be selected such that adequate amounts of antigen-stimulated lymphocytes are formed.

B. Obtaining the spleens or lymph nodes of the immunized mammals and preparation of a spleen cell suspension or a lymph node cell suspension in a suitable medium.

C. Fusion of the suspended spleen cells or lymph node cells with myeloma cells of a suitable cell line (for example NS1-Ag 4/1 myeloma cells), using a suitable fusion promoter (for example polyethylene glycol). A ration of about 10 spleen cells or lymph cells per myeloma cell is preferred. A total volume of about 1 ml of fusion medium is adequate for $10^8$ spleen cells or lymph node cells. The myeloma cell line used should preferably be of the so-called "drug resistant" type, so that, in a selective medium, unfused myeloma cells die whilst hybrids survive. Cell lines resistant to 8-azaguanine, which cells lack the enzyme hypoxanthine-guanine phosphoribosyl transferase and which therefore cannot grow in a HAT medium (hypoxanthine, aminopterine, thymidine), are most frequently used.

The myeloma cell line used should also preferably be of the "non-secreting" type so that it does not itself form anitbodies or H or L chains of immunoglobulins.

D. Dilution and cultivation in individual vessels of the unfused spleen cells or lymph node cells, the unfused myeloma cells do not divide so that the unfused cells die (about 1–2 weeks). The individual fused cells are isolated by adjusting the volume of the diluent so that a given number of cells (about 1–4) is placed in each individual vessel (for example each well of a microtitre plate). The medium (for example HAT medium) prevents the growth of the resistant (for example against 8-azaguanine) unfused myeloma cell line, and thus it dies. The unfused spleen cells or lymph node cells have only a limited number of division cycles and hence these cells also die after a certain period (about 1–2 weeks). In contrast, the fused cells continue to divide since they have inherited permanent growth from the parent myeloma cells and the ability to synthesize the enzyme hypoxanthine-guanine phosphoribosyltransferase from the parent spleen cells or lymph node cells, and thus they are able to survive in the selective medium.

E. Checking for the presence of antibodies against plasminogen activator inhibitor in each vessel.

F. Selecting (for example by limiting dilution) and cloning the hybridomas which produce the desired antibody.

When the desired hybridoma has been selected and cloned monoclonal antibodies of very high purity are obtained when the hybridomas are cultured in a suitable medium for a certain time and the antibody is obtained and purified form the supernatant. A suitable medium and the optimum culture time can easily be determined. This in vitro technique provides monoclonal antibodies which are contaminated with only small amounts of proteins from the heterologous serum (for example fetal calf serum).

In order to produce a significantly higher concentration of monoclonal antibodies of only very slightly reduced purity, the selected hybridoma can be injected into a, preferably syngeneic or semisyngeneic, mouse. After a certain incubation time, this leads to the formation of a tumour in the mouse which releases high concentrations of antibody (5–20 mg/ml) in the blood and in the peritoneal exudate (ascites) of the host animal. Even though these mice have normal antibodies in the blood and ascites, nevertheless thses only arise at a concentration of about 5% of the monoclonal antibodies.

According to the nomenclature recommended by the Subcomittee on Fibrinolysis of the International Comittee on Thrombosis and Hemostasis, Jun. 8, 1986, endothelial type plasminogen activator inhibitor (e-PAI) should br denominated plasminogen activator inhibitor type 1 (PAI-1). In the following description and Example 6–9, this nomenclature has been used.

Prognostic Significance of PAI-1 in Extracts from Human Tumours

Since it is well established that proteolytic activity is necessary for tumour cell spreading, molecules involved in the regulation of invasion and metastasis are attractive as prognostic/diagnostic tools. The challenge is to identify those patients at low risk and those at high risk of recurrence. An accurate means of distinguishing those at high or low risk of relapse would spare patients at low risk from severe side effects of adjuvantchemotherapy while high risk patients could be offered intensive chemotherapy.

Beast Cancer

Foucre et al. (1991) Br. J. 64, 926–932, found a 74-fold increase of PAI-1 in breast tumours as compared with normal breast tissue. Similar findings were reported by Sumiyoshi et al., 1991 who also found that increased levels of tumour PAI-1 were directly proportional to the number of tumour positive axillary lymph nodes.

Jänicke et al. (1991) Sem. Throm. Hemostasis 17, 303–312, were the first to describe the prognostic role of PAI-1 in breast tumour extracts. Including tumour extracts from 113 breast cancer patients, high tumour PAI-1 content as determined by a sandwich ELISA, was shown to be an independent and significant predictor of poor prognosis. Two later studies by Grøndahl-Hansen et al. (1993) Cancer Res. 53, 2513–2521, including 190 patients and by Foekens et al. (1994) J. Clin. Oncol. 12, 1648–1658, including 657 patients, confirmed the prognostic impact of PAI-1 in patients with node negative and node positive breast cancer.

Of particular interest is that PAI-1 seems to be independent prognostic variable, i.e. measurement of tumour PAI-1 content contributes significantly to the prognostic information which can be obtained by other prognostic parameters. For example, in the subgroup of patients with estrogen receptor negative tumours, PAI-1 tumour measurements allows for a further prognostic stratification (Grøndahl-Hansen et al., supra). Also in the subgroup of patients with 1 to 3 tumour positive axillary lymph nodes, PAI-1 could be used to separate the patients into significantly different prognostic groups (Grøndahl-Hansen et al., supra). This latter observation suggests that in the group of patients with 1–3 tumour positive lymph nodes a subgroup of high-risk patients can be identified and these women might be offered more intensive chemotherapy.

In the study by Foekens et al., supra, PAI-1 appeared to be the strongest biochemical prognostic marker, when uPA, cathepsin D, pS2, estrogen and progesterone receptors were included as the other biochemical variables, indicating the importance of PAI-1 measurements in predicting prognosis in breast cancer.

Gastric Cancer

Analyzing PAI-1 tumour content in 76 patients with complete resection of their gastric cancer, Nekarda et al. (1994) Cancer Res. 54, 2900–2907, were able to demonstrate prognostic significance of PAI-1, high PAI-1 being significantly associated with poor prognosis when using the best cut-off value to part the patients in two groups, 45 patients having low values and 31 having high. In a multivariate Cox regression analysis, PAI-1 was proven to be an independent prognostic factor with nodal status and WHO-classification as the two only other prognostic factors.

Pancreatic Cancer

Applying immunohistochemistry on paraffine sections. Takeuchi et al. (1993) Am. J. Gastroenterology 88, 1928–1933, studied the prognostic role of tumour PAI-1 and PAI-2 staining intensity in 97 patients with pancreatic cancer. While strong staining intensity for PAI-2 was significantly associated with long overall survival, PAI-1 staining intensity had no impact on survival.

Colon Cancer

Tumour PAI-1 levels as levels as measured by ELISA, are found significantly elevated in primary colon adenocarcinomas and their metastasis as compared to normal colon mucosa: normal mucosa<primary tumour>liver metastasis (Sier et al. [1994] Gastroenterology 107, 1449–1456). The authors conclude that the high PAI-1 content in colorectal cancer metastasis in the liver is associated with an inactivation of the enhanced urokinase cascade, which might allow tumour cells to settle in the liver. Ganesh et al. (1994) Cancer Res. 54, 4065–4071, studied the prognostic impact of PAI-1 in 92 colon carcinomas and found no significant correlation between PAI-1 as determined by sandwich ELISA, and patient outcome.

In a recent study performed at the Finsen Laboratory (unpublished), PAI-1 content was investigated by ELISA in normal colon mucosa, in the periphery of colon adenocarcinomas and in the center of the tumours. Normal mucosa had approximately 10 fold less than PAI-1 than the periphery of the tumour, while the center of the tumour had approximately 50 fold higher PAI-1 levels than the normal mucosa. When comparing tumour PAI-1 levels with clinical outcome in the relative low number of patients, a trend towards statistical significance is survival between high versus low PAI-1 was seen (FIG. 6).

Lung Cancer

In a retrospective study including tumour tissue from 106 lung adenocarcinoma patients we determined PAI-1 by sandwich ELISA. Using the upper and lower quartiles as cut-off points, high PAI-1 was shown to be significantly ($P=0.017$) correlated with short overall survival (Pedersen et al. [1994] Cancer Res. 54, 120–123). In Cox multivariate analysis, including clinical parameters and tumour uPA, PAI-1 was shown to be an independent prognostic marker for survival, stage being the only other significant prognostic factor. When analyzing the 69 stage 1 patients separately and using the median as cut-off point, high levels of PAI-1 were significantly (P=0.038) associated with poor prognosis.

In a second retrospective study including tumour tissue from 84 patients with squamous cell lung cancer and 38 patients with large cell lung cancer (Pedersen et al. [1994], Cancer Res. 54, 4671–4675), there was a non-significant trend towards high PAI-1 levels being associated with poor prognosis in squamous cell lung cancer. However, combining high tumour levels of PAI-1 and high tumour levels of urokinase type plasminogen receptor (27 of the 84 patients), a highly significant (P=0.008) association with short survival was seen. PAI-1 did not have any significant correlation with survival in the group of large cell lung cancer patients (Pedersen et al., supra).

Ovarian Cancer

A number of studies have shown that tumour concentration of PAI-1 in ovarian cancers is significantly higher as compared with benign ovarian tissue specimens (Casslén et al. [1994] Eur. J. Cancer, 1302–1309; Kuhn et al. [1995] Gy. Oncol., in press).

In a recent study by Kuhn et al., supra, PAI-1 as determined by ELISA was shown to predict survival in advanced ovarian cancer patients after radical surgery and platinum-based chemotherapy, i.e. high tumour levels of PAI-1 was significantly (P=0.01) associated with short survival. A best cut-off point was defined dividing the patients into 27 with low level and 24 with high PAI-1 tumour levels. In the multi-variate analysis residual tumour after operation and high PAI-1 or high uPA were the only prognostic factors.

Plasma PAI-1

All studies published until now on the prognostic value of PAI-1 are based on determinations in tumour extracts. For most types of cancer, the development of more effective diagnostic methods has resulted in earlier detection and thus smaller tumour size at the time of surgery. This is making it increasingly difficult to acquire access to frozen, unfixed tumour samples. Therefore, the conversion of the PAI-1 assay from a tumour extract based test to one that can analyze plasma samples, would significantly increase its clinical use. Sample collection would be much easier and less invasive.

PAI-1 can be detected in plasma and has been shown to be elevated in patients with pancreatic cancer (Sandberg et al. [1992] 69, 2884–2887), ovarian cancer (Casslén et al., supra) and in urinary tract cancers (Bashar et al. [1994] Urol. Int. 52, 4–8). In the last study, plasma levels are significantly higher in a group of patients with metastatic disease than in patients without distant metastasis. An association between the degree of cancer cell atypia and plasma PAI-1 levels was reported.

In a recent study performed at the Finsen Laboratory (unpublished), it was found that patients with colon adenocarcinomas preoperatively had increased plasma PAI-1 levels as compared to healthy control individuals. A correlation was found between tumour and plasma PAI-1 content in the individual patients, and subsequent correlation to survival showed significant different survival among patients with low versus high plasma PAI-1 content (FIG. 7).

In breast cancer patients, we have also recently been able to show an increased plasma PAI-1 level in the cancer patients as compared to healthy controls.

Diagnostic Significance of Plasma PAI-1 in Human Cancer

Follow-up of patients in either surgically or medically induced remission most often involves only clinical examination. With the high recurrence rate in many cancer types, a sensitive diagnostic assay, e.g. an assay as outlined in Example 6, which is capable of identifying non-clinically evident recurrence will be of significant value.

Colon Cancer

It has recently been observed that in patients with advanced colon adenocarcinomas (Dukes D) plasma PAI-1 levels are correlated with tumour burden, e.g. high plasma PAI-1 level before debulking surgery, significant fall post-operatively and then steady increase during disease progression (FIG. 8) (unpublished data).

In its broadest aspect, the invention relates to a method of predicting the presence or progression of a malignant tumour in a subject having or suspected of having a malignant tumour, the method comprising (a) determining at a first point in time (I) one or more of PAI-1 DNA abundance, PAI-1 mRNA abundance, or PAI-1 protein abundance in tumour tissue or a sample of a body fluid such as plasma, serum or urine from said subject, (b) determining at a later point in time (II) one or more of PAI-1 DNA abundance, PAI=1 mRNA abundance, or PAI-1 protein abundance in a sample of body fluid from said subject, (c) determining the difference between the abundance of said PAI-1 DNA, PAI-1 mRNA, or PAI-1 protein determined at said first point in time (I) with the value determined at said later point in time (II), and (d) correlating said difference with an established level of difference which is indicative of a high likelihood of tumour presence or metastasis.

In particular, the invention relates to a method wherein said first point in time (I) is preoperatively, and said second point in time (II) is at least 2 weeks postoperatively, such as 4, 6 or 8 weeks or even 3, 6, 12, 18 or 24 months postoperatively. It is contemplated that if the difference between the abundance of said PAI-1 DNA, PAI-1 mRNA, or PAI-1 protein determined at said first point in time (I) and the value determined at said later point in time (II) is more than 50% of the value determined at the first point in time (I), such as 75% or 100% or more, this is indicative of a non-clinically (and possibly also clinically) evident recurrence.

In a specific embodiment, the method comprises the steps of:

(a) testing a tissue section from a malignant tumour or a sample of a body fluid from a patient suspected of having a malignant tumour, said sample taken at a first point in time (I), with an antibody reagent specific for PAI-1 protein under antibody binding conditions, (b) determining the binding of the reagent to PAI-1 protein in said tissue section or sample of a body fluid taken at said first point in time (I), (c) testing a sample of a body fluid from a patient suspected of having a malignant tumour, said sample taken at a later point in time (II), with an antibody reagent specific for PAI-1 protein under antibody binding conditions, (d) determining the binding of the reagent to PAI-1 protein in said sample of body fluid taken at said later point in time (II), (e) determining the difference between the level of said PAI-1 protein determined at said first point in time (I) with the value determined at said later point in time (II), and (f) correlating said difference with an established level of difference which is indicative of a high likelihood of tumour presence or metastasis.

By the term "antibody reagents" is meant whole antibodies and parts thereof, either alone or conjugated with other moieties. Antibodies include polyclonal antibodies, monoclonal antibodies, and single chain antibodies. Antibody fragments are those that bind the PAI-1 protein, including Fab and $F(ab)_2$ fragments, inter alia. The antibody reagents may comprise antibodies made in animals or by recombinant DNA techniques. Also the antibody reagents include antibody and antibody fragments conjugated to, among other moieties, detectable labels, such as enzymatic labels and fluorescent labels. Other useful labels which may be comprised by the antibody reagents include radionucleotides.

Antibody binding conditions are generally well known in the art and, for the most part, will include neutral pH, moderate salt, temperatures between 2–3° C., incubation times between several minutes and overnight or longer. Preferred conditions include those described in Examples 6–9.

It will be readily appreciated by those of ordinary skill in the art that the details of an antibody binding procedure may be adjusted to favour improved signal to noise ratios or sensitivity, rapidity or completeness, and the like. Moreover, conditions may be adjusted to accomodate different histological procedures for fixation and staining. Finally, it will be appreciated that titers and appropriate dilutions will be different for different antibody reagent preparations.

In a presently preferred embodiment of the above method, said antibody reagent is an antibody according to the invention and the determination of the PAI-1 protein level is performed by using an immunoassay, such as an ELISA or RIA, or by using an activity assay.

In yet another embodiment of the present invention, the abundance of PAI-1 mRNA or PAI-1 DNA in a tumour tissue sample may be detected by in situ hybridization using PAI-1 sequence specific probes, or by hybridization of PAI-1 sequence specific probes to mRNA or DNA from normal and tumour tissue.

In a still further embodiment of the present invention, the polymerase chain reaction ("PCR") is used to detect PAI-1 DNA or mRNA in a tumour tissue sample.

In another embodiment, RNA ("Northern") blotting may be used in the methods of the invention. According to this method, RNA is isolated from tumour tissue by any of a number of standard procedures.

Predictive value of tumour PAI-1 in human cancer.

As shown in Example 6, a proportion of colon adenorcarcinoma cancer patients have high levels of plasma PAI-1 which predict a poor prognosis. Accordingly, patients with high PAI-1 levels will be candidates for anti-PAI-1 therapy treatment. Example 7 describes a predictive assay to identify patients who will potentially benefit from such a treatment.

The invention further relates to a method of predicting the prognosis of an individual subject having or suspected of having a malignant tumour, the method comprising a) determining the level of PAI-1 DNA abundance, PAI-1 mRNA abundance, or PAI-1 protein abundance in malignant or potentially malignant tissue or another sample, such as plasma, serum, or urine, from a number of subjects having or suspected of having a malignant tumour, b) establishing a threshold level of PAI-1 DNA, PAI-1 or PAI-1 protein above or equal to which a value is indicative of a high likelihood of non-clinically evident tumour metastasis resulting in a poor prognosis, c) correlating the level of PAI-1 DNA, PAI-1 mRNA or PAI-1 protein of the individual subject with the value established in b) in order to determine the prognosis of the individual subject, and optionally d) if the likelihood of a poor prognosis is high, allocating the individual subject to subsequent antineoplastic treatment.

Whether a prognosis is good or poor depends upon the likelihood or metastasis. A "high likelihood" of tumour metastasis means that there is more than 40% risk of tumour metastasis within about five years.

Another aspect of the invention relates to a method of selecting a subject having or suspected of having a malignant tumour for anti-PAI-1 treatment, the method comprising a) determining the level of PAI-1 DNA abundance, PAI-1 mRNA abundance, or PAI-1 protein abundance in malignant or potentially malignant tissue or another sample, such as plasma, serum, or urine, from the subject, b) correlating said value with an established threshold level determined as described above, and c) selecting for anti-PAI-1 treatment patients having a PAI-1 level above or equal to the pre-determined threshold level.

The above diagnostic, prognostic and predictive methods may be applied to samples from any subject having or suspected of having a malignant tumour, e.g. to samples from a subject or patient who has been established to have a carcinoma in situ.

In certain embodiments of the above methods, the subject or patient is a patient who has been established to have a high risk of developing a malignant tumour by having a high-risk-indicating score of a tumour marker such as a serum/plasma tumour marker or by having a gene or gene product which indicates that the patient is at high risk of developing a malignant tumour; the malignant tumour being selected from the group consisting of mammary carcinomas, urological carcinomas e.g. prostrate carcinoma and bladder carcinoma, gynaecological carcinomas e.g. ovarian carcinoma and cervical carcinoma, non-small cell lung tumours, gastrointestinal cancers, e.g. colon adenocarcinoma, and gastric cancers, brain tumours, sarcomas, haematological malignancy e.g. lymphoma and skin cancers e.g. melanoma and squamous cell skin cancer.

Prognostic value of uPA:PAI-1 complexes in patients with breast cancer

Tumour content of uPA, PAI-1 and uPAR has been shown to predict prognosis in breast cancer (Foekens et al., Foekens et al., Grøndahl-Hansen et al., Grøndahl-Hansen et al.). These studies have been based on measurement of total amounts of uPA, uPAR or PAI-1. It is well known, however, that both uPA and PAI-1 can exist in active and inactive forms (pro-uPA, uPA, latent PAI-1, active PAI-1). Active PAI-1, which is present in surplus in breast cancer tissue (J änicke et al.), will from complexes with uPA but not with pro-uPA (Andreasen et al.). The uPA:PAI-1 complex can bind uPAR and is internalized when uPAR bound (Nykjær et al.). Tumour content of (active) uPA which might be an indicator of active proteolysis per se in the tumour tissue constitutes only a small fraction of the total amount of uPA (Skriver et al.). There are at present no ELISA methods for a selective determination of (active) uPA. Since active PAI-1 only forms complexes with (active) uPA and not with pro-uPA, the amount of uPA:PAI-1 complexes could represent an indirect measure of active uPA in a tissue and thereby a measure of active proteolysis.

Based on monoclonal and polyclonal uPA and PAI-1 antibodies, an ELISA which with high sensitivity detects complexes between uPA and PAI-1, cf. Example 8 (FIG. 9) and a standard material consisting of in vitro form uPA:PAI-1 complexes have been developed.

Figure 10:
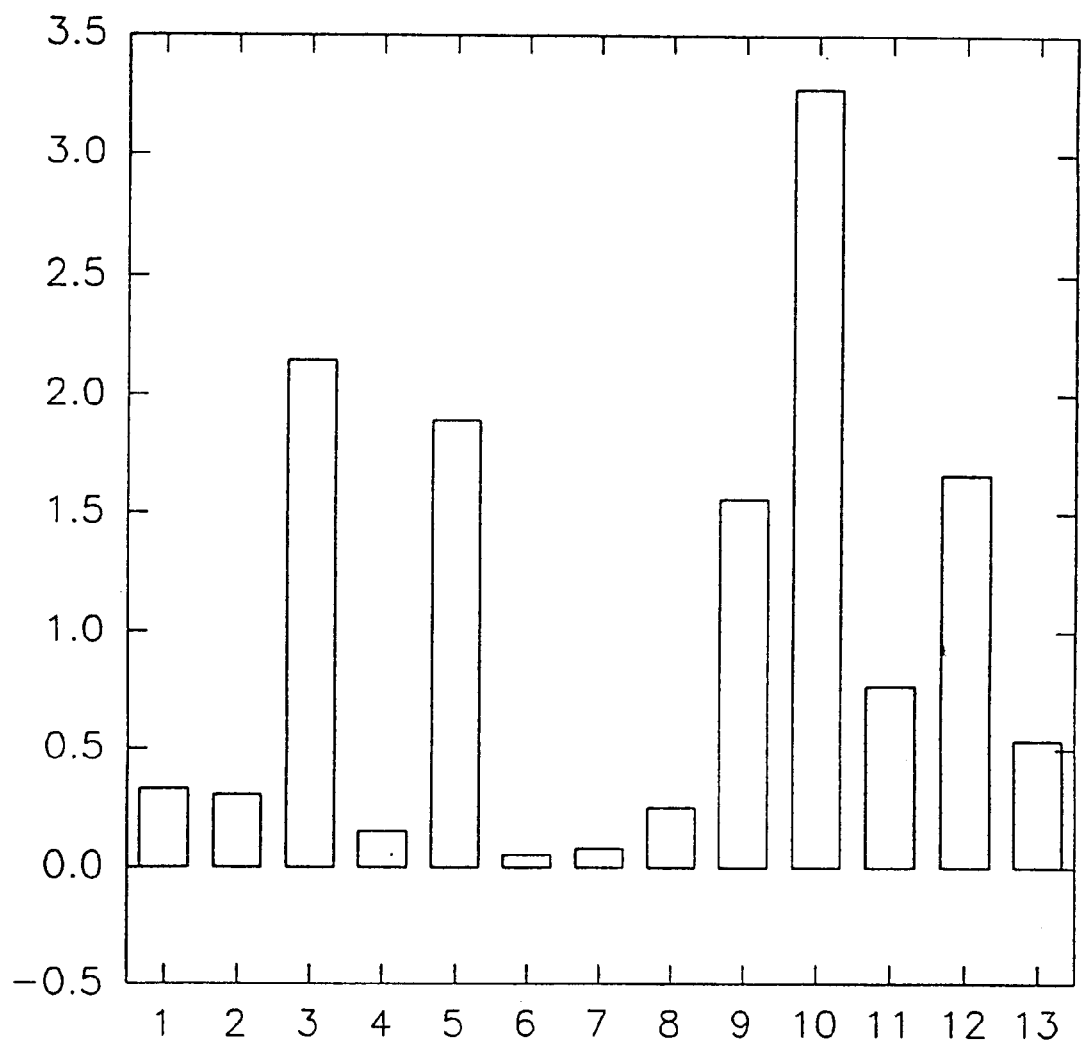
FIG. 10 shows the absorbance of a uPA:PAI-1 complex ELISA measuring uPA:PAI-1 complexes in 13 breast cancer cytosols.

A sensitive and specific uPA:PAI-1 complex ELISA and a stable uPA:PAI-1 complex standard preparation have been developed as described in Example 8. By measuring complexes in breast cancer cytosols, immunoreactivity was found in all samples with large variations between the samples (FIG. 10). A number of validation studies on the ELISA are currently being performed, including the use of different tumour extraction procedures. Upon completion of these studies, a breast cancer cytosol bank will be used to determine the exact prognostic value of uPA:PAI-1 complexes.

Similarly, the prognostic value of uPA:PAI-1 complexes is tested in extracts from other cancer types, e.g. colon, non-small cell lung cancer, gastric cancer, ovarian cancer, and cervical cancer. Also, the presence of uPA:PAI-1 complexes in plasma, serum, and urine from cancer patients is examined for a prognostic value in a similar manner as the experiments described in Examples 6 and 7.

A further aspect of the invention thus relates to a method of predicting the presence or progression of a malignant tumour in a subject having or suspected of having a malignant tumour, the method comprising (a) determining at a first point in time (I) uPA:PAI-1 complexes in tumour tissue or a sample of a body fluid such as plasma, serum or urine from said subject, (b) determining at a later point in time (II) uPA:PAI-1 complexes in a sample of body fluid from said subject, (c) determining the difference between the abundance of said uPA:PAI-1 complexes determined at said first point in time (I) with the abundance determined at said later point in time (II), and (d) correlating said difference with an established level of difference which is indicative of a high likelihood of tumour presence or metastasis.

The method will generally comprise the following step:

(a) testing a tissue section from a malignant tumour or a sample of a body fluid from a patient suspected of having a malignant tumour, said sample taken at a first point in time (I), with an antibody reagent specific for uPA:PAI-1 complexes under antibody binding conditions, (b) determining the binding of the reagent to uPA:PAI-1 complexes in said tissue section or sample of a body fluid taken at said first point in time (I), (c) testing a sample of a body fluid from a patient suspected of having a malignant tumour, said sample taken at a later point in time (II), with an antibody reagent specific for uPA:PAI-1 complexes under antibody binding conditions, (d) determining the binding of the reagent to uPA:PAI-1 complexes in said sample of body fluid taken at said later point in time (II), and (e) determining the difference between the level of said uPA:PAI-1 complexes determined at said first point in time (I) with the value determined at said later point in time (II), and (f) correlating said difference with an established level of difference which is indicative of a high likelihood of tumour presence or metastasis.

In a preferred embodiment, the determination of the uPA:PAI-1 complexes is performed by using an immunoassay, such as an ELISA or RIA, or by using an activity assay or other assays as described in further detail above with regard to PAI-1 assays.

In another aspect, the invention relates to a method predicting the prognosis of an individual subject having or suspected of having a malignant tumour, the method comprising a) determining the level of uPA:PAI-1 complexes in malignant or potentially malignant tissue or another sample, such as plasma, serum, or urine, from a number of subjects having or suspected of having a malignant tumour, b) establishing a threshold level of uPA:PAI-1 complexes above or equal to which a value is indicative of a high likelihood of non-clinically evident tumour metastasis resulting in a poor prognosis, c) correlating the level of uPA:PAI-1 complexes of the individual subject with the value established in b) in order to determine the prognosis of the individual subject, and optionally d) if the likelihood of a poor prognosis is high, allocating the individual subject to subsequent antineoplastic treatment.

The invention also encompass a method of selecting a subject having or suspected of having a malignant tumour for anti-PAI-1 treatment, the method comprising a) determining the level of uPA:PAI-1 complexes in malignant or potentially malignant tissue or another sample, such as plasma, serum, or urine, from the subject, b) correlating said value with an established threshold level determined as described above, and c) selecting for anti-PAI-1 treatment patients having a uPA:PAI-1 complexes level above or equal to the predetermined threshold level.

EXAMPLES

The invention will be described in further detail with reference to the examples. Examples 1 to 5 illustrate the production and use of monoclonal antibodies against an endothelial type plasminogen activator inhibitor (e-PAI) released into the culture fluid from dexamethasone-treated human fibrosarcoma cells. The inhibitor inhibits human urokinase-type plasminogen activator (u-PA) and tissue-type plasminogen activator (t-PA).

Example 1

Production of the antigen used for immunization

Inhibitor was purified from serum-free conditioned culture fluid of dexamethasone-treated human fibrosarcoma cells of the line HT-1080 ) ATCC CCL221) by a procedure adapted from that described by van Mourik, J. A., Lawrence, D. A., and Loskutoff, D. J. (1984) J. Biol. Chem. 259, 14914–14921 for the plasminogen activator inhibitor from bovine endothelial cells. The HT-1080 cell line was maintained as a monolayer culture, using Dulbecco-modified Eagle's medium supplemented with 10% fetal bovine serum. Serum-free culture fluid was prepared from confluent monolayer cultures. Dexamethasone, a synthetic glucocorticoid, was added to the serum-free cultures in a concentration of 10–6 M. HT-1080 cells produce relatively high amounts of u-PA, which under the culture conditions used is in the proenzyme form. Before purification of inhibitor, the culture fluid was depleted of u-PA by passing it through a column of monoclonal anti-u-PA IgG immobilized on Sepharose (Nielsen, L. S., Hansen, J. G., Skriver, L., Wilson, E. L., Kaltoft, K., Zeuthen, J., and Danø, K. (1982) Bio-chemistry, 24, 6410–6415). The culture fluid was then applied to a column of concanavalin A-Sepharose equilibrated with 0.01 M sodium phosphate, pH 7.4, 0.15 M NaCl (PBS), at a flow rate of 30 ml per h, using 5 ml Concanavalin A-Sepharose per liter culture fluid. The column was washed with 5 column volumes of PBS with 0.3 M NaCl. Bound protein was eluted with PBS with 0.5 M NaCl and 0.2 M a-methyl-D-mannoside. Fractions containing the peak of protein, as determined by measuring the absorbancy at 280 nm, were pooled and used for further analysis.

From photometric scanning at 600 nm of Coomassie Blue stained polyacrylamide gels, the partly purified preparation was estimated to contain approximately 75% of a Mr/54,000 protein, the electrophoretic mobility of which coincided with inhibitory activity as determined by reverse zymography (see below). Before immunization this preparation was dialysed against PBS.

Immunization of BALB/c-mice

4 BALB/c-mice were immunized intradermally with approximately 20 μg of the Mr/54,000 protein obtained above in Freund's incomplete adjuvant on day 0, 7, 14, and 21. The plasma of each mouse was analyzed by ELISA (Enzyme Linked Immunosorbent Assay) and the mouse showing the highest titer against the immunization preparation was chosen for intraveneous injection and fusion with myeloma cells. The intraveneous injection of a similar dose as above dissolved in PBS was given on day 28 and the spleen was removed 3 days later.

Cell fusion and culture of cells

Spleen cells were mixed with NSI-Ag 4/1 myeloma cells (resistant to 0.1 mM 6-thioguanine; synthesize but do not secrete kappa light chains) (Köhler and Milstein (1976) Eur. J. Immunol. 6, 511–519) in a ratio of 10:1 (108 spleen cells to 107 NSI-Ag 4/1 cells) and incubated with 1 ml of 50% (wt/vol) polyethylene glycol in a phosphate-buffered saline solution for 90 sec. at 37° C. Dulbecco's modified Eagle's medium (20 ml) was added to the suspension, and the cells were centrifuged at 1000×g. The cell pellet was resuspended in 96 ml of hypoxanthine/aminopterin/thymidine medium (Littlefield, J. W. (1964) Science 145, 709–710) supplemented with 10% fetal bovine serum and was distributed in 48 wells of Costar trays (Costar, Cambridge, M. A.). The medium was changed twice weekly.

Selection of hybridomas

For screening of hybridoma supernatants using ELISA (Enzyme Linked Immunosorbent Assay), wells of Immuno Plates were coated with 100 μl per well of concanavalin A-Sepharose-purified plasminogen activator inhibitor containing/4 mg of protein per ml in 0.1 M Na2CO3, pH 9.8 overnight at 37° C. In order to block residual binding sites, the wells were incubated with 0.25% BSA in PBS for more than 15 minutes. Then the wells were incubated with hybridoma supernatants for 1 hour and finally with peroxidase-conjugated rabbit antibodies against mouse Ig (Dakopatts, Copenhagen, Denmark), diluted 1:800 in PBS with 0.1% Tween 20 for 1 hour. Peroxidase reaction was performed for 5 min. with 100 ml of 0.1% o-phenylenediamine, 0.01% H202 in 0.1 M citrate-phosphate, pH 5.0. The reaction was stopped by the addition of 100 ml of 1 M $H_2SO_4$, and absorbancy was read at 492 nm.

For screening by immunoblotting, proteins in 10 ml of serum-free medium from HT-1080 cells were concentrated by precipitation with trichloracetic acid and separated by SDS-PAGE in a 10 cm wide lane. The proteins were transferred electrophoretically (10 V, 250 mA for 16 h at room temperature) from the polyacrylamide gel to nitrocellulose paper. The transfer buffer used was 0.125 M Tris HCl, 0.19 M glycine, 20% (v/v) methanol, 0.1% (w/v) SDS, pH 8.6. The nitrocellulose paper was washed in 0.05 M Tris HCl, pH 7.4 0.15 M NaCl, 1% Triton X-100 (TBS-Triton) for 15 min. at room temperature and incubated for 30 min. with TBS-Triton containing human serum albumin (10 mg/ml). The paper was then washed 2×15 min. in TBS-Triton. Vertical lanes were cut out and incubated over-night at 4° C. with culture supernatants from the hybridomas. The lanes were washed in TBS-Triton for 3×15 min., incubated for 1 h at room temperature with peroxidase-conjugated rabbit IgG anti-mouse immunoglobulins (diluted 1:50 in TBS-Triton), and washed for 3×10 min. in 0.05 M Tris-HCl, pH 7.6. The peroxidase reaction was then performed with 0.5 mg/ml of di-aminobenzidine in 0.01% $H_2O_2$ for 5 min. at room temperature.

As a control nitrocellulose lanes were incubated with supernatant from hybridomas (Hy 2.15) producing antibody of irrelevant specificity (anti-trinitrophenyl) (Shulman, M., Wilde, C. D., and Köhler, G. (1978) Nature, 276, 269).

After 10 days of cultivation of the hybridomas supernatant from 16 primary wells showed a strongly positive ELISA reaction. The hybridomas from said wells were cloned and recloned by limiting dilution (Kennett, R. H., McKearn, J. T., and Bechtol, K. B. (1980) Monoclonal Antibodies. Hybridomas: A New Dimension in Biological Analysis (Plenuim, N.Y.)). After cloning and recloning 4 stable ELISA-positive clones remained. Immunoblotting analysis showed that all four clones produced antibody which reacted with an Mr/54,000 band in crude conditioned culture fluid from HT-1080 cells.

Purification of antibodies

Monoclonal antibodies produced by the 4 clones obtained were purified from hybridoma culture fluid on a protein A-Sepharose column as follows: 200 μl of conditioned culture fluid from hybridomas was applied to a 5 ml protein A-Sepharose column (12×43 mm). The column was washed with 30 ml of 0.1 M Tris HCl, pH 8.1. Elution was performed with 0.1 M sodium acetate, pH 4.0 0.15 M NaCl. Fractions of 2 ml were collected in tubes containing 200 μl of 1 M Tris-HCl, pH 9.0. The IgG concentration in the purified preparation was determined by spectrophotometry at 280 nm (A280 nm 1%=14). Concentrations of IgG in impure solutions were determined by single radial immunodiffusion using purified mouse IgG as a standard.

Characterisation of the antibodies produced by the cloned hybridomas

The classes and subclasses of the antibodies produced by the hybrid clones were analysed by immunodiffusion against class-and subclass-specific goat antibodies (Meloy, V. A., U.S.A.). All 4 antibodies produced by the 4 clones were of the $IgG_1$ sub-class.

Isoelectric focusing of the 4 purified monoclonal antibodies in slab gels containing 6% polyacrylamide and 6% carrier ampholyte solution (Pharmalyte) showed that their isoelectric points were different (ranging between 5 and 7.5). The binding characteristics of the antibodies to solid-phase inhibitor as measured by ELISA differed greatly. They were therefore considered to originate from different hybridization events. The four clones were designated anti-plasminogen activator inhibitor clone 1, 2, 3, and 4, respectively.

All four clones have been deposited, under the Budapest Treaty, as follows:

| PAI-1 Clone | Depository/Accession No. | Date |
|---|---|---|
| 1 | ECACC 00112117 | November 21, 2000 |
| 2 | DSM ACC 2489 | January 25, 2001 |
|   | ECACC 01010303 | January 3, 2001 |
| 3 | DSM ACC 2490 | January 25, 2001 |
|   | ECACC 01010304 | January 3, 2001 |
| 4 | ECACC 00112120 | November 21, 2000 |

The full name and address of the depositories are

DSM: Deutsche Sammlung von Mikroorganismen and Zellkulturen, Mascheroder Weg 1b, D-38124 Braunschweig GERMANY;

ECACC: European Collection of Animal Cell Cultures, Centre for Applied Microbiology & Research, Salisbury, Wiltshire SP4OJG, United Kingdom.

The deposited material will be made available in accordance with U.S. law, in particular, 37 CFR §1.808 (a) and (b).

Cross-reaction of antibodies against plasminogen activator inhibitor from human fibrosarcoma cells with other plasminogen activator inhibitors.

Conditioned culture fluid from human umbilical cord endothelial cells also contains a plasminogen activator inhibitor detectable by reverse fibrin-agarose zymography (Sprengers, E. O., Verheijen, J. H., van Hindsberg, V. W. M., and Emeis, J. J. (1984) Biochim. Biophys. Acta. 801, 163–170). This inhibitor has an electrophoretic mobility indistinguishable from that of the HT-1080-inhibitor. FIG. 1 is a zymogram showing reverse zymography for plasminogen activator inhibitor in culture fluid conditioned by HT-1080 cells (a–c) or umbilical cord endothelial cells (d–f) before (a, d) and after passage or Sepharose columns coupled with monoclonal antibodies against TNP (b, e) and against HT-1080 plasminogen activator inhibitor (c, e). For coupling procedure see Example 2. Two one ml columns containing approximately 1 mg of monoclonal anti-TNP IgG and monoclonal anti-plasminogen activator inhibitor IgG from clone 1, respectively, were equilibrated with a buffer containing 0.1 M Tris HCl, pH 8.1, 0.1% Triton X-100. To both columns was added 1 ml of serum-free cell culture fluid from HT-1080 cells and the run-through was collected. Serum-free cell culture fluid from human umbilical cord endothelial cells was treated identically. After electrophoresis, the gel was processed for reverse zymography for plasminogen activator inhibitors with an incubation period of 1.5 hours. Reverse zymography was carried out as described by Eriksson, L. A., Lawrence, D. A., and Loskutoff, D. J. (1984) Anal. Biochem. 137, 454–463. Plasminogen activator inhibitors in SDS polyacrylamide gels are detected by layering the gels over agarose gels containing fibrin, plasminogen, and plasminogen activator. Inhibitors diffuse into the fibrin/plasminogen/plasminogen activator gel from the polyacrylamide gel, and their presence is revealed by zones of fibrin resistant to plasminogen activator-catalyzed lysis. The position of Mr-markers are indicated.

Passage of HT-1080 medium through the Sepharose column with antibodies from anti-inhibitor IgG clone 1 removed the inhibitory activity as revealed by reverse fibrin-agarose zymography; there was no effect of passage through a control column with a monoclonal control antibody (anti-TNP IgG). When plasminogen activator inhibitor from said human endothelial cells are applied to the column with monoclonal antibodies from clone 1 the inhibitor is bound to the column (FIG. 1). When columns with the antibodies from clone 2, 3, or 4 were used, the results were identical (results not shown). This demonstrates immunological similarities between this inhibitor and the HT-1080 plasminogen activator inhibitor.

Using the same technique, it has been shown that rabbit antibodies against the HT-1080-inhibitor cross-react with a plasminogen activator inhibitor extracted from human blood platelets prepared by the method described by Erikson, L. A., Ginsberg, M. H., and Loskutoff, D. J. (1984), J. Clin. Invest., 74, 1465–1472.

It has been reported that the endothelial cell plasminogen activator inhibitor, the platelet inhibitor (Erikson, L. A., Ginsberg, M. H., and Loskutoff, D. J. (1984), J. Clin. Invest., 74, 1465—1472) and the inhibitor from rat hepatoma cells of the HTC line show immunological similarities (D. J. Loskutoff and T. D. Gelehrter, personal communication). Thus it appears that the HT-1080-inhibitor is similar to a number of plasminogen activator inhibitors isolated from different cells and tissues.

Example 2

Immunosorbent purification of inhibitor

After coupling to Sepharose, antibody produced by anti-plasminogen activator inhibitor clone 1 was used for purification of inhibitor from HT-1080 cell culture fluid by a column procedure. 8 mg of monoclonal antibodies from anti-inhibitor IgG clone 1 was coupled to 2 ml of cyanogen bromide-activated Sepharose 4B. The material was packed in a column (20×16 mm), which was equilibrated with 0.1 M Tris HCl, pH 8.1. Conditioned cell culture fluid from HT-1080 cells was applied at a flow rate of 50 ml/hr. The column was washed with equilibration buffer (flow rate 50 ml/hr) follow by 0.1 M Tris HCl, pH 8.1, 1 M NaCl (flow rate 50 ml/hr.) Elution was performed at a flow rate of 25 ml/h with 0.1 M $Ch_3COOH$, pH 2.7, collecting fractions of 2 ml into tubes containing 200 ml of 1 M Tris HCl, pH 9, 0 in order to neutralize the eluate. Fractions containing protein as determined by absorbance measurements at 280 nm were pooled.

For quantification of inhibitory activity 0.005 Ploug Units urokinase standard in 25 ml of assay buffer was mixed with 25 ml of inhibitor diluted in the same buffer; this mixture was diluted to 500 ml with assay buffer added to [$^{125}$I]-fibrin plate wells (see Example 3). From assays with fixed concentrations of urokinase standard and serial dilutions of inhibitor preparations, the dilution or inhibitor causing 50% inhibition of the urokinase standard was calculated. The amount of inhibitor in wells with 50% inhibition was defined as 0.0025 inhibitor unit (Inh.U.). Before assay, inhibitor preparations were treated with SDS to a final concentration of 0.1%, and after a one hour incubation at 25° C., Triton X-100 was added to a final concentration of 1%.

Results from the purification of inhibitor from human fibro-sarcoma cells are shown in Table I.

TABLE 1

Purification of inhibitor from human fibrosarcoma cells by monoclonal antibody coupled to Sepharose

| Fraction | Volume ml | Protein mg | Total inhibitory activity Inh. Units | Specific inhibitory activity Inh. Units/mg | Yield % |
|---|---|---|---|---|---|
| Conditioned culture fluid applied to column | 740 | 59.9 | 19,200 | 321 | 100 |
| Run through | 740 | ND | 2,600 | ND | 14 |
| Wash 1 | 10 | ND | ND | ND | ND |
| Wash 2 | 40 | ND | ND | ND | ND |
| Eluate | 14.2 | 1.14 | 16,400 | 14,400 | 85 |

Figure 2:
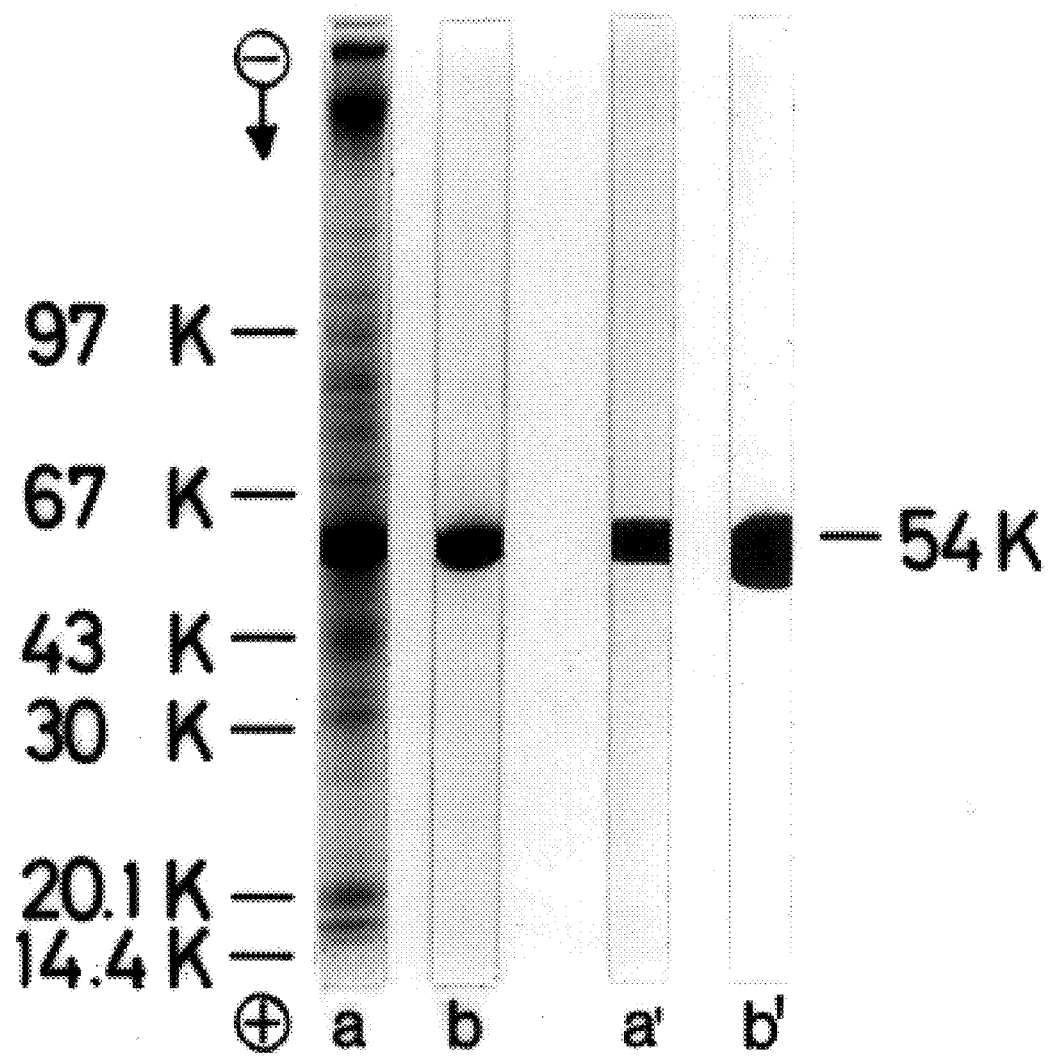
FIG. 2 is a photography showing SDS-PAGE and reverse fibrin agarose zymography of HT-1080 cell medium and e-PAI purified by immunoabsorbent chromatography with a monoclonal antibody against e-PAI.

As shown in Table I, 86% of the inhibitory activity was bound by the column. After washing 99% of the inhibitory activity bound to the column could be eluted at low pH. A 45-fold purification of inhibitory activity was obtained and the eluate contained only an Mr/54,000 protein band as evaluated by Coomassie Blue staining of a SDS-polyacrylamide gel. The electrophoretic mobility of this protein coincided with the mobility of inhibitory activity as determined by reverse fibrin-agarose zymography (FIG. 2). The samples subjected to SDS-polyacrylamide gel electrophoresis (SDS-PAGE) were: 1.5 ml crude culture fluid from HT-1080 cells (a), eluate corresponding to 10 mg of protein (b), 10 ml of crude culture fluid from HT-1080 cells (a'), and eluate corresponding to 50 ng of protein (b'). After electrophoresis, the gels were either stained with Coomassie Blue (a, b), or inhibitor in the gels was visualized by reverse fibrin agarose zymography for 2 hours (a', b'). The position of the following markers are indicated: Rabbit phosphorylase b (97 K), Bovine serum albumin (67 K), ovalbumin (43 K), carbonic anhydrase (30 K), soybean trypsin inhibitor (20.1 K), and α-lactalbumin (14.4 K).

As judged from spectrophotometric scannings of stained polyacrylamide gels with crude culture fluid and the purified preparation, the strong Mr/54,000 band was purified to the same extent as the inhibitory activity. SDS-PAGE in slab gels with a 6–16% linear concentration gradient of polyacrylamide of crude culture fluid and run-through from the immunosorbent column showed that the Mr/54,000 band was greatly diminished, while no other bands were affected (results not shown).

SDS-PAGE under reducing conditions showed one band with Mr/54,000, indicating that the purified inhibitor consisted of one polypeptide chain (results not shown).

Example 3

Neutralization of inhibitory activity

Figure 3:
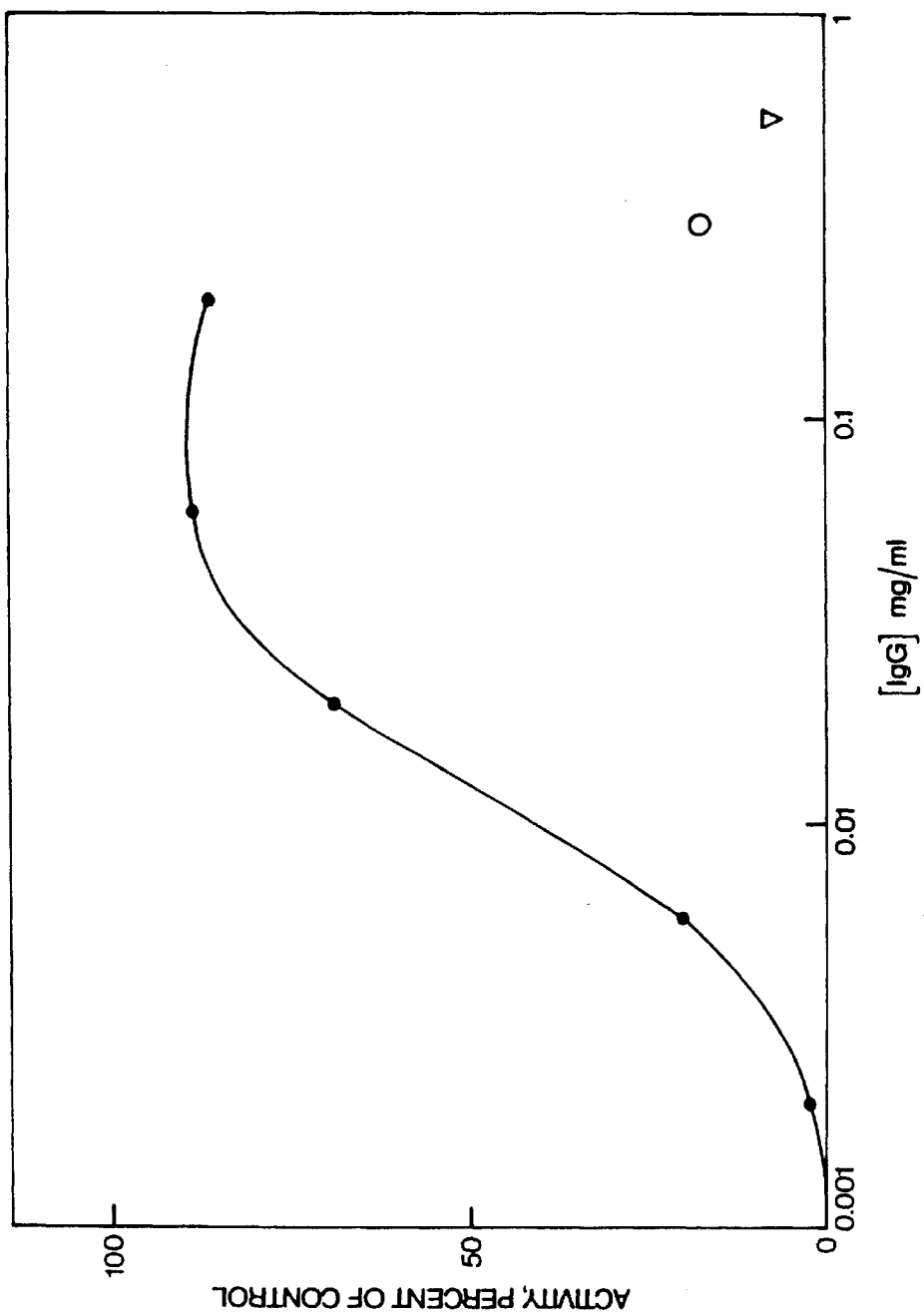
FIG. 3 is a graph showing neutralization of inhibitory action of e-PAI by monoclonal antibody against e-PAI.

The effect of the monoclonal antibodies on the inhibitory activity of the inhibitor was tested by a +125I(-fibrin plate assay, which involved the activation of plasminogen by u-PA and the subsequent degradation of +125I(-fibrin by the plasmin formed (cf. Nielsen L. S., Hansen, J. G., Andreasen, P. A., Skriver, L., Danø, K., and Zeuthen, J. (1983) EMBO J., 2, 115–119). The +125I(-fibrin plate assay was carried out as follows: 10 ng of inhibitor was added to +125I(-fibrin plate assay wells together with 0.2 ng active u-PA, 1 mg of Glu-plasminogen and IgG as indicated, in a total volume of 500 ml of 0.1 M Tris HCl, pH 8.1, 0.1% Triton X-100, 0.25% gelatine (assay buffer). Radioactivity released in parallel control assays without u-PA (approximately 500 cpm) was subtracted and the radioactivity released in the presence of inhibitor calculated as a percentage of that released in the absence of inhibitor (approximately 3000 cpm). The total radioactivity in the +125I(-fibrin plate assay wells was approximately 60,000 cpm. Each point represents the mean of two determinations. A neutralization of inhibitory activity that increased with increasing concentrations of anti-inhibitor IgG from clone 2 was observed (FIG. 3, (●)) while there was no significant effect on inhibition of antibodies from clone 1 (FIG. 3 (o)) and the monoclonal control antibody of irrelevant specificity (anti-TNP IgG) FIG. 3 (Δ)). No neutralizing effect was observed with anti-inhibitor IgG from clone 3 and 4 (results not shown).

Example 4

Binding of uPA/inhibitor complexes to monoclonal anti-inhibitor antibodies.

Figure 4:
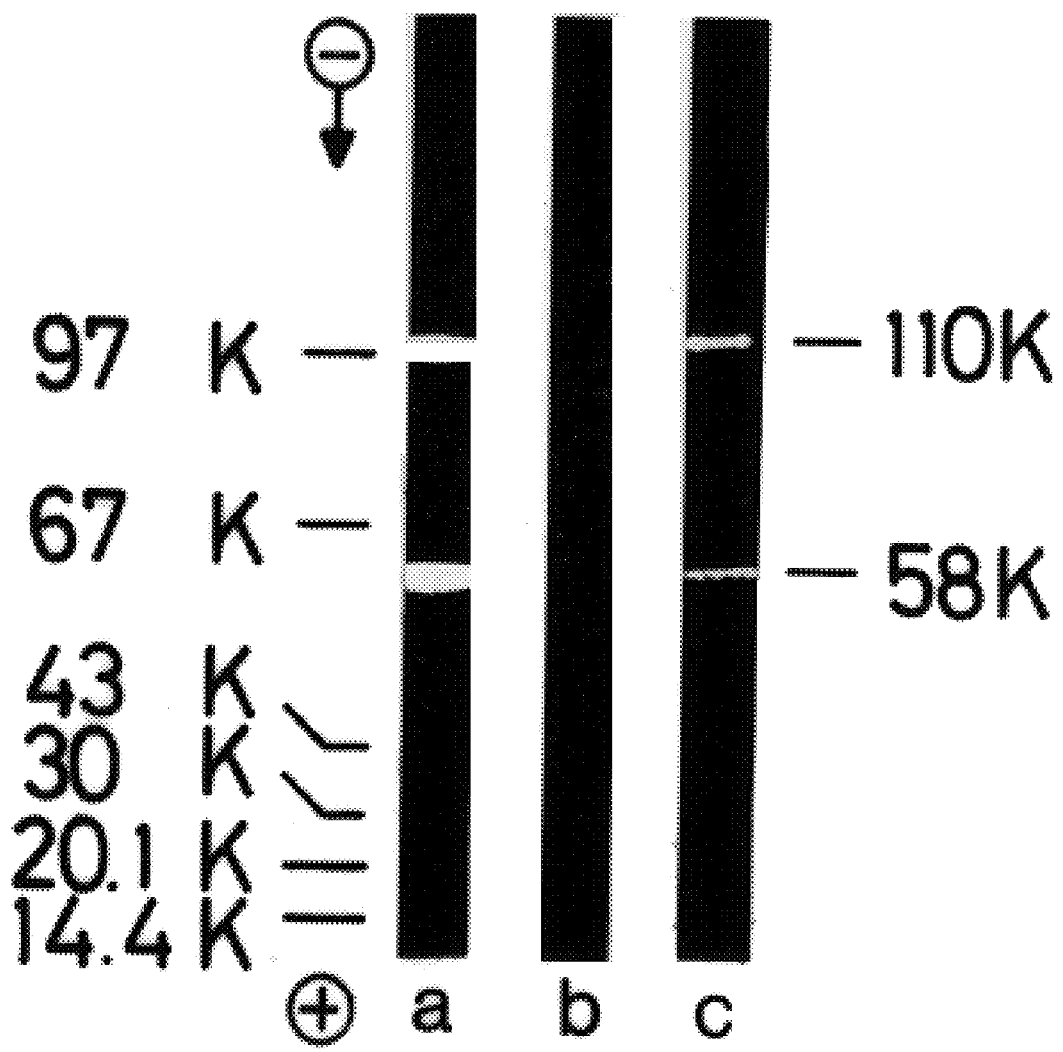
FIG. 4 is a zymogram showing binding of complexes of u-PA with e-PAI to Sepharose columns with monoclonal antibodies against e-PAI.

It has been shown that u-PA forms an equimolar complex with the HT-1080 inhibitor. This complex has an electrophoretic mobility corresponding to Mr/100,000 in SDS-PAGE and is detectable because it regains its plasminogen activator activity as measured by fibrin-agarose zymography: Plasminogen activator activity in poly acrylamide gels is detected by layering the gels over agarose gels containing fibrin and plasminogen—the plasminogen activators diffuse into the agarose gels and activate plasminogen to produce visible lysis zones (Granelli-Piperno, A. and Reich, E. (1978) J. Exp. Med., 148, 223-14 234). FIG. 4 is a zymogram showing the binding of complexes of u-PA and HT-1080-inhibitor to Sepharose columns with monoclonal antibodies against the HT-1080 inhibitor. One ml columns containing approximately 1 mg of monocolonal anti-TNP antibody (a), antibodies from anti-inhibitor IgG clone 1 (b), or monoclonal anti-plasminogen activator inhibitor IgG from clone 2 (c) were equilibrated with a buffer containing 0.1 M Tris HCl, pH 8.1, 0.1% Triton X-100, 0.25% gelatin. One ml u-PA-inhibitor complex obtained by incubating the activator (25 ng/ml) with the inhibitor (500 ng/ml) for 1 h at 25° C. in a buffer of 0.1 M Tris-HCl, pH 8.1, 0.1% Triton X-100 was added to each column, and 75 ml of the run—through from each column was subjected to SDS-PAGE followed by zymography for plasminogen activators. The positions of Mr-markers are indicated. Antibodies from anti-inhibitor clone 2 bound these complexes, while no binding was observed with antibodies from anti-inhibitor clone 1 or anti-TNP. Likewise, monoclonal anti-plasminogen activator inhibitor IgG from clone 4 bound complexes, while antibodies from 3 did not (results not shown). Said differential reactivities can be used in quantitation of free versus complex-bound inhibitor.

Example 5

Immunocytochemical localization of the inhibitor

The monoclonal anti-plasminogen activator inhibitor antibodies can be used for immunocytochemical localization of the inhibitor in normal or malignant cells and tissues.

Figure 5:
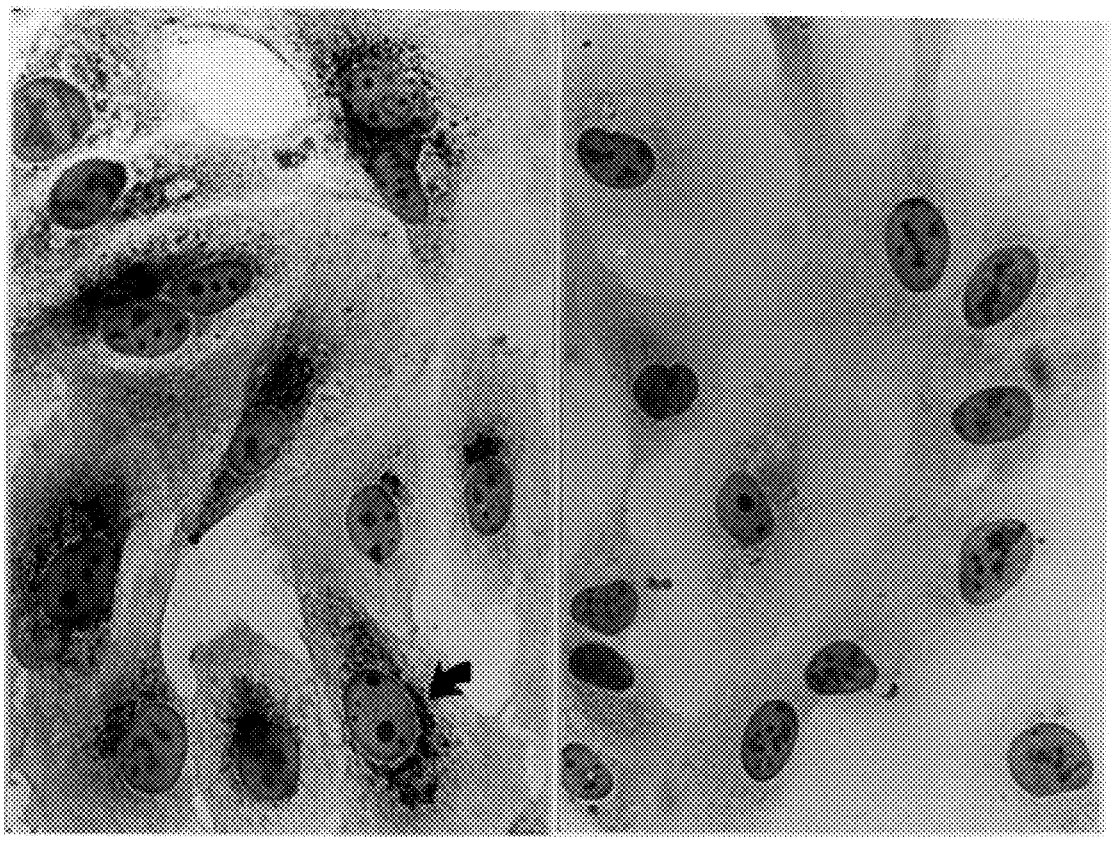
FIG. 5 is a photography showing immunoperoxidase staining of HT-1080 cells with a monoclonal antibody against e-PAI.

HT-1080 cells cultured in serum free medium in the presence of dexamethasone were seeded on microscope slides and fixed for 30 min. with 4% paraformaldehyde in 0.1 M sodium phosphate buffer, pH 7.3. After washing with 0.05 M Tris-HCl, pH 7.4, 0.15 M NaCl (TBS) containing 1% Triton X-100 TBS-Triton) for 30 min., the cells were exposed to 10% rabbit serum in TBS for 30 min. and incubated overnight at 4° C. with purified monoclonal antibody (10 mg/ml) diluted in TBS with 10% rabbit serum. Following a 1 h temperature requilibration, the cells were washed with TBS-Triton and bound monoclonal antibody was demonstrated by incubation with peroxidase conjugated rabbit anti-mouse IgG (1:60) diluted in TBS with 10% rabbit-serum followed by development with diaminobenzidine-hydrogen peroxide. The cells were lightly counterstained with haematoxylin, dehydrated, mounted and photographed. A strong granular staining was observed often with a perinuclear localization together with a weak diffuse staining apparently distributed in the entire cytoplasm (FIG. 5, top). A distinct granular staining was observed using antibody from all 4 clones (results shown for clone 1 only). When the monoclonal anti-inhibitor antibody was substituted by monoclonal IgG of irrelevant specificity (anti-TNP antibody) (FIG. 5, bottom) or by buffer alone, no staining was seen.

The invention has been illustrated with reference to the production and use of monoclonal antibodies against a Mr/54,000 plasminogen activator inhibitor released into the culture fluid from dexamethasone-treated human fibrosarcoma cells, but since said inhibitor is immunologically similar to the plasminogen activator inhibitors derived from human endothelial cells, human platelets and rat hepatoma cells, it should be understood that monoclonal antibodies against plasminogen activator inhibitors from these sources and plasminogen activator inhibitors which are immunologically similar to the plasminogen activator inhibitors from any of these sources also fall within the scope of the invention.

Example 6

Prognostic value of plasma PAI-1 in patients with colorectal cancer

All studies published until now on the prognostic value of PAI-1 in cancer are based on determinations in tumour extracts. For most types of cancer, the development of more effective diagnostic methods has resulted in earlier detection and thus smaller tumour size at the time of surgery. This makes it increasingly difficult to gain access to frozen, unfixed tumour samples. If similar prognostic information as that obtained by analyzing tumour extracts could be obtained by a preoperatively collected plasma sample, it would significantly increase its clinical value with sample collection being easier and less invasive.

Colon cancer affects one out of twenty in the U.S. and in most Westernized countries. With more than 155,000 new cases diagnosed each year, this disease accounts for 15% of all cancers and constitutes a major public health problem. The disease is divided according Dukes' stage A–D. Recently, adjuvant chemotherapeutic treatment of patients with Duke' C has been recommended. However, a large fraction of these patients, who are cured by the primary surgical treatment, will still receive chemotherapy. A reliable means of selecting those patients at highest risk of recurrence would allow for adjuvant therapy to be limited to this group and thus spare a large number of patients from the often severe side effects associated with chemotherapy.

MATERIALS AND METHODS

Patients

The patients from whom the plasma samples were drawn all had surgery for colorectal cancer. Patients were follow regularly in the out-patient department. Survival data were obtained from the Central Danish Registry of Death.

Plasma sampling

Plasma was obtained from 609 patients with colorectal cancer. The plasma was collected preoperatively and stored at −80° C. until analyzed for PAI-1 content.

PAI-1 ELISA

PAI-1 was determined using a sandwich ELISA (Gro/ndahl-Hansen et al., 1993, "High levels of urokinase-type plasminogen activator (u-PA) and its inhibitor PAI-1 in cytosolic extracts of breast carcinomas are associated with poor prognosis"; Cancer Research 53, 1513–1521) with monoclonal catching and detecting antibodies. As catching antibody was used PAI-1 monoclonal antibody clone 1, and as detecting antibody was used PAI-1 monoclonal antibody clone 7. This assay detects both latent and active PAI-1 and in addition recognizes PAI-1 bound to uPA and tPA (unpublished results, J. Grøndahl-Hansen). PAI-1 was measured as ng/mg protein.

Statistical methods

The patients were randomly divided into two groups, each of which being representative for the total number of patients. The first group of patients (293 patients) were used to search for an optimum cut-off value to separate patients into two groups with different survival. This optimized cut-point was then tested in the second group of patients (316 patients).

Results

Figure 7A:
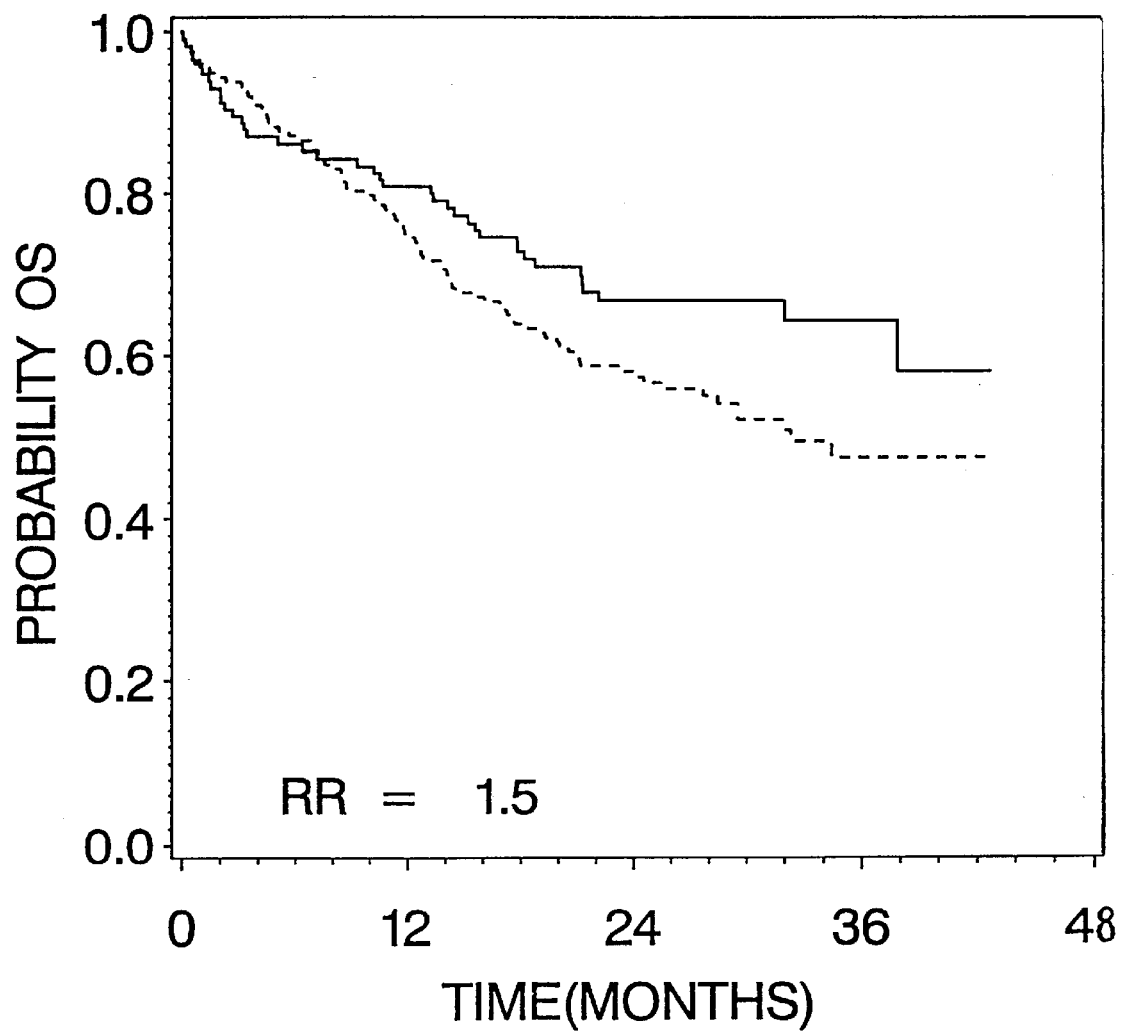
FIG. 7A shows univariate survival curves of 293 with colon cancer; patients were divided according to an optimized plasma PAI-1 cut-off value (0.58 ng/mg protein); OS=overall survival, RR=relative risk, and the numbers indicate number of patients at risk.

The optimized plasma PAI-1 cut-off value was calculated to be 0.58 ng/mg protein. Using this cut-off point in the 293 patients gave a relative hazard rate of 1.5, i.e. patients with plasma PAI-1 levels above this cut-off point had a 50% higher risk of death than patients with plasma PAI-1 levels below the cut-off point (FIG. 7A).

Figure 7B:
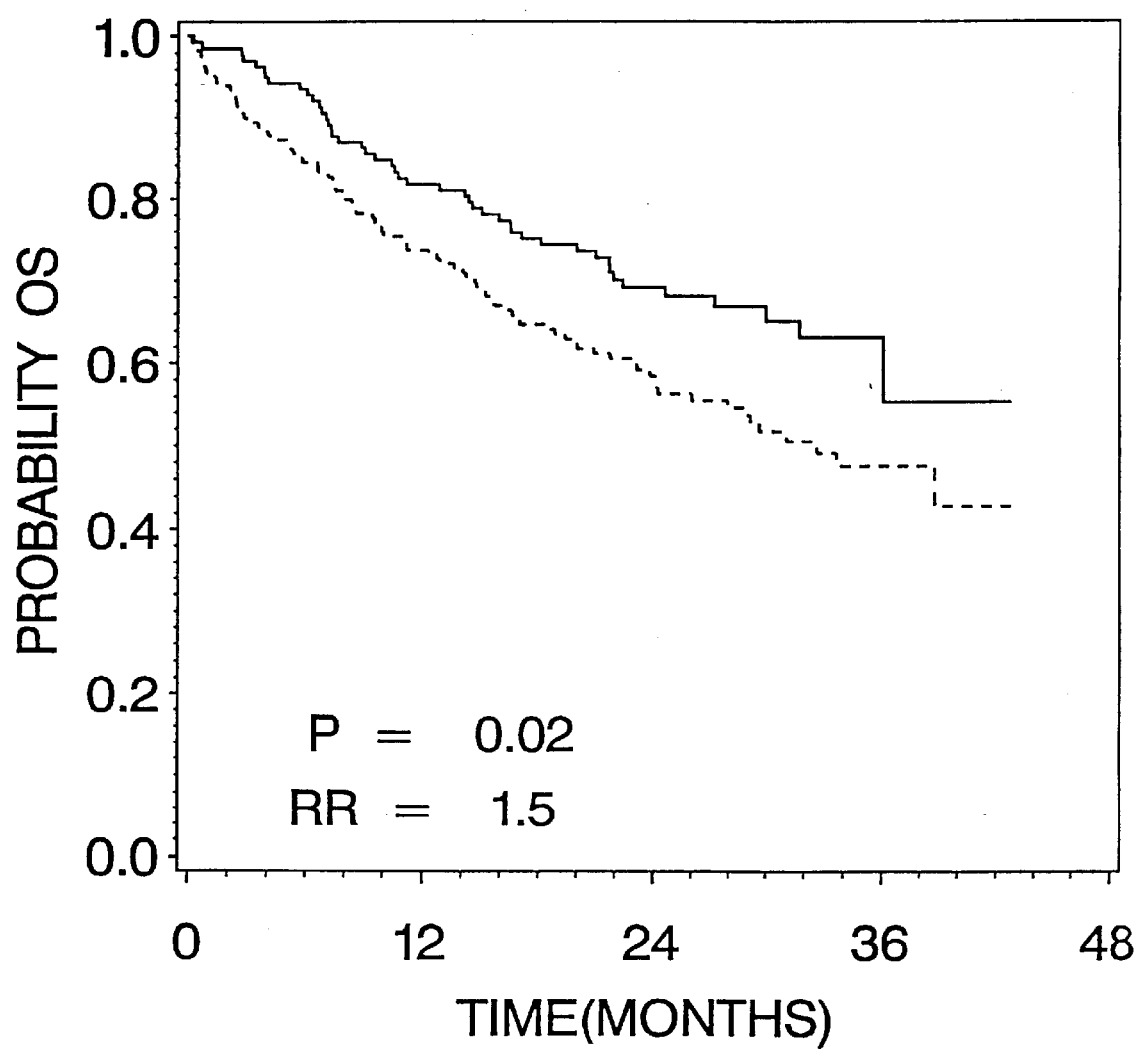
FIG. 7B shows univariate survival curves of 316 patients with colon cancer; patients were divided according to the optimized plasma cut-off value calculated from the first data set of 293 patients (FIG. 7A); OS=overall survival, RR=relative risk, and the numbers indicate number of patients at risk.

Applying the optimized cut-off point on the group of 316 patients gave identical results (FIG. 7B).

DISCUSSION

This study of the prognostic value of preoperative plasma PAI-1 in patients undergoing surgical resection for colorectal cancer suggests that high plasma levels of PAI-1 are associated with short overall survival. Measurement of plasma PAI-1 might then be used to divide colorectal cancer patients into groups of low versus high risk of recurrence. Only patients at high risk of recurrence should then be offered adjuvant systemic chemotherapy. The present study is the first of its kind, and the prognostic value of plasma PAI-1 in other types of cancer can and should be evaluated in a similar manner.

Example 7

Predictive test of plasma PAI-1 measurements in patients having colon adenocarcinomas.

In this example is described a predictive test to identify patients who should be offered anti-PAI-1 therapy.

MATERIALS AND METHODS

Patients

Patients with colon adenocarcinoma Dukes' B+C referred for adjuvant therapy subsequent to radical resection of their tumours.

PAI-1 ELISA

Plasma samples from the patients with colon adenocarcinoma is stored at −80° C.

PAI-1 is determined using a sandwich ELISA (Gro/ndahl-Hansen et al., 1993) with monoclonal catching and detecting antibodies. As catching antibody is used PAI-1 monoclonal antibody clone 1 and as detecting antibody is used PAI-1 monoclonal antibody clone 7 (WO 87/00549). This assay detects both latent and active PAI-1, and is in addition recognizing PAI-1 bound to uPA and tPA (unpublished results, J. Grøndahl-Hansen). PAI-1 is measured in interim units by calibration with standard preparations obtained from The National Institute for Biological Standards and Control, Hertfordshire, UK. The intra- and intervariations for both assays are below 11%.

TREATMENT

The patients are divided into groups on the basis of their tumour or plasma PAI-1 content. All patients in the groups having a high tumor and/or plasma PAI-1 content will receive anti-PAI-1 treatment. Clinical responses will be recorded according to standard procedures (EORTC). Patients will be post-stratified according to tumour and/or plasma PAI-1 content (patients with tumor PAI-1 levels at or above versus below the established median value of 0.775 InterimU/mg protein and patients with plasma PAI-1 levels on or above the established median value of 0.58 ng/mg protein in serum) and number and duration of objective responses as well as survival will be compared between groups of patients.

Example 8

Diagnostic value of plasma PAI-1 in patients with colorectal cancer.

Follow-up cancer patients in either surgically or medically induced remission most often involves only clinical examination. With the high recurrence rate in many cancer types, a sensitive diagnostic assay which is capable, with high sensitivity, of identifying non-clinically evident recurrence will be of significant value. Such a test might also be useful in screening high-risk populations for the occurrence of cancer.

MATERIALS AND METHODS

Patients

The patients from whom the plasma samples were collected all had surgery for colorectal cancer. Patients were followed regularly in the out-patient department.

Plasma sampling

Plasma was obtained preoperatively, peroperatively, on days 2 and 7 postoperatively and then every three months until clinical relapse was evident. PAI-1 ELISA The PAI-1 ELISA was performed as described above in Example 6.

Results

Figure 8A:
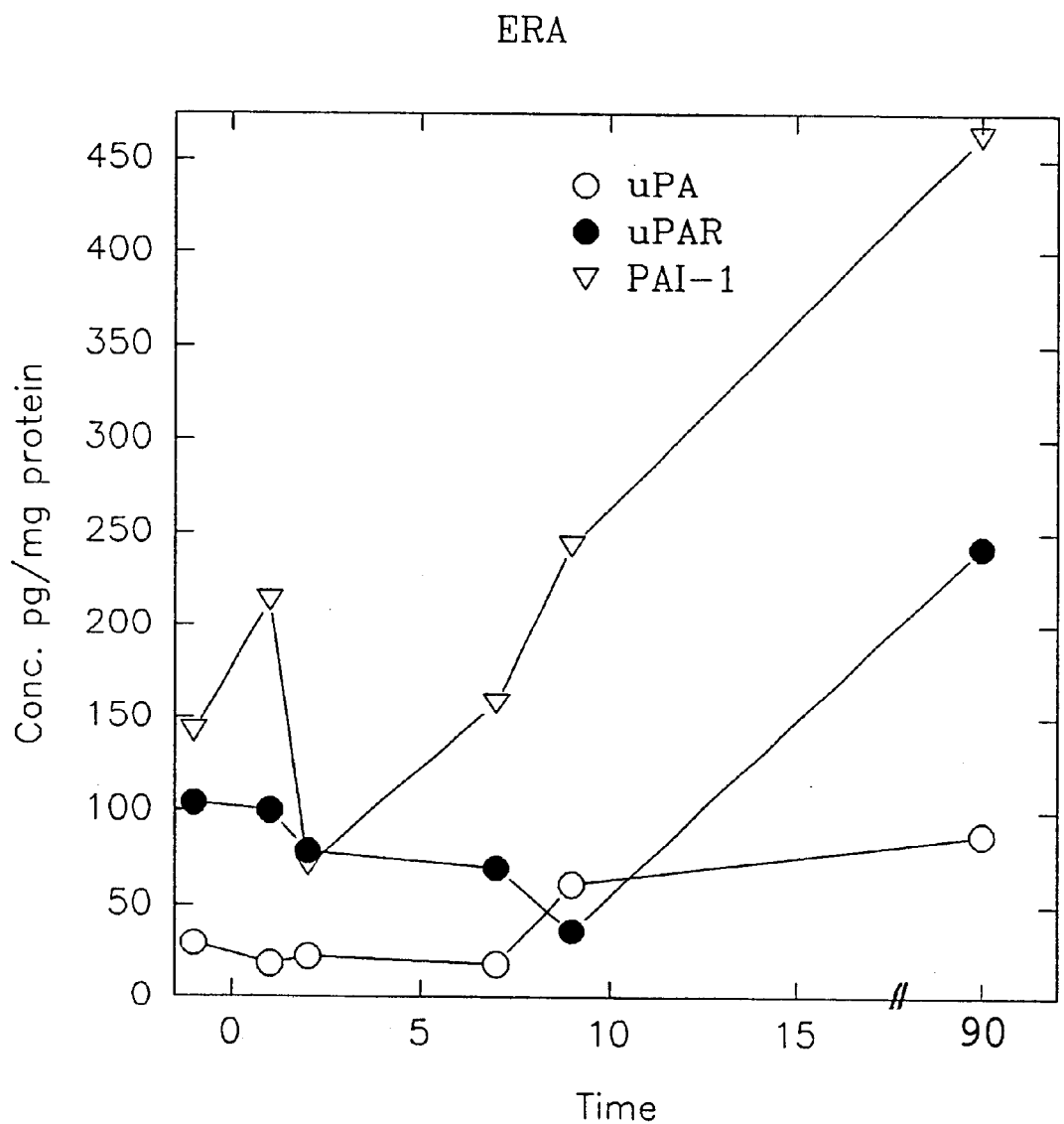
FIG. 8A shows plasma uPA, uPAR, and PAI-1 levels in a patient who had complete resection of her primary colon cancer and who did not experience relapse.
Figure 8B:
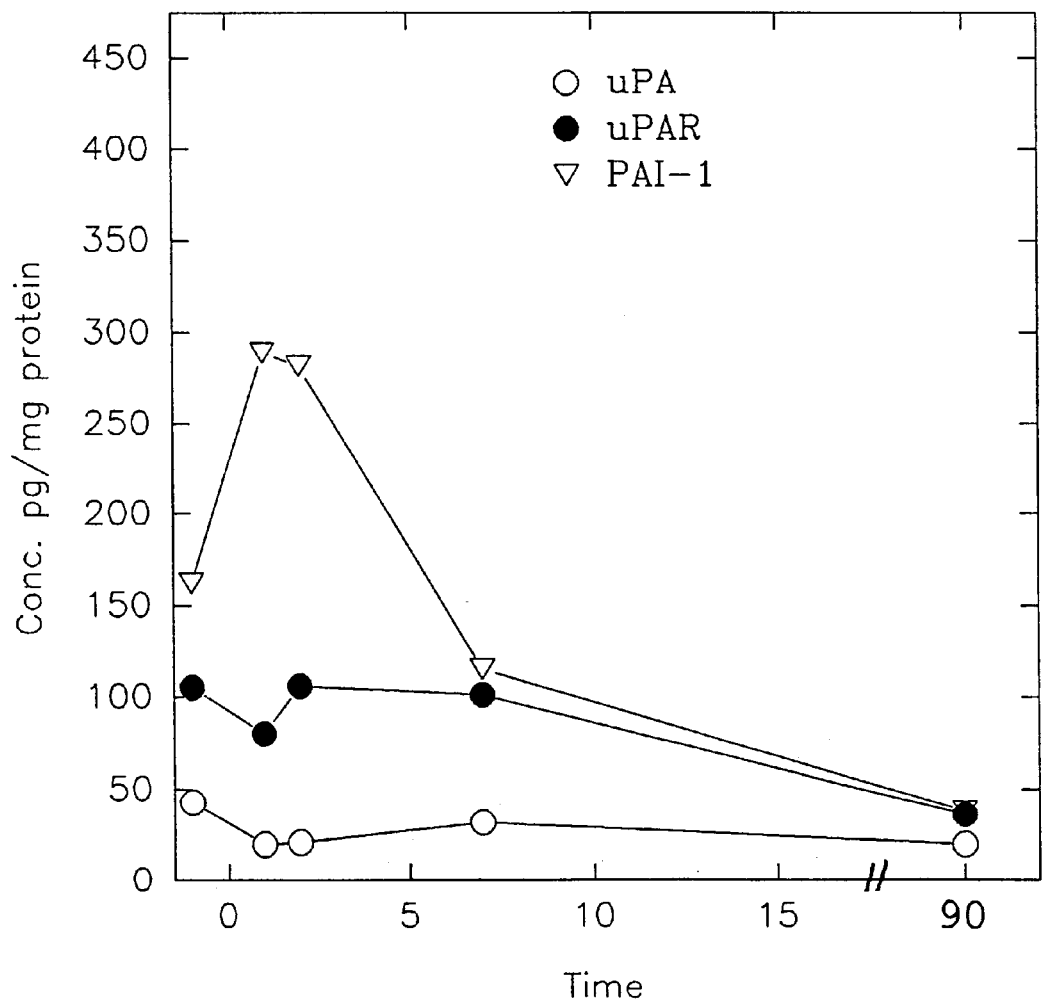
FIG. 8B shows plasma uPA, uPAR, and PAI-1 levels in a patient who had complete resection of her primary colon cancer and who did not experience relapse.

FIG. 8A shows plasma uPA, uPAR and PAI-1 levels in a patient with progressive colorectal cancer. At the time of surgery, the patient had no signs of disseminated disease. The preoperative plasma PAI-1 level was elevated, but decreased as a result of surgical removal of the primary tumour. However, at 3 months follow-up, PAI-1 had increased 3 times over the preoperative plasma PAI-1 value, and the patient now presented clinically evident liver metastasis. FIG. 8B shows plasma uPA, uPAR and PAI-1 from a patient who had her primary colon cancer removed and who did not experience a relapse of her cancer. The preoperative plasma PAI-1 value was elevated, but decreased subsequent to surgery. During the 3-month follow-up period, no increase in plasma PAI-1 was observed, which is consistent with no appearance of metastasis.

DISCUSSION

This study on patients with colorectal cancer suggests that measurement of plasma PAI-1 might be used as a marker for relapse of the cancer disease. Routine measurement of plasma PAI-1 might then be used to follow patients who have achieved a surgically or medically induced complete remission of their colorectal cancer. In many cancer diseases, early detection of a relapse is a prerequisite for a subsequent curative therapy. Therefore, the diagnostic value of plasma PAI-1 in other types of cancer should be evaluated in a similar manner.

Example 9

Determination of uPA:PAI-1 complexes in patients

MATERIALS AND METHODS

Figure 9:
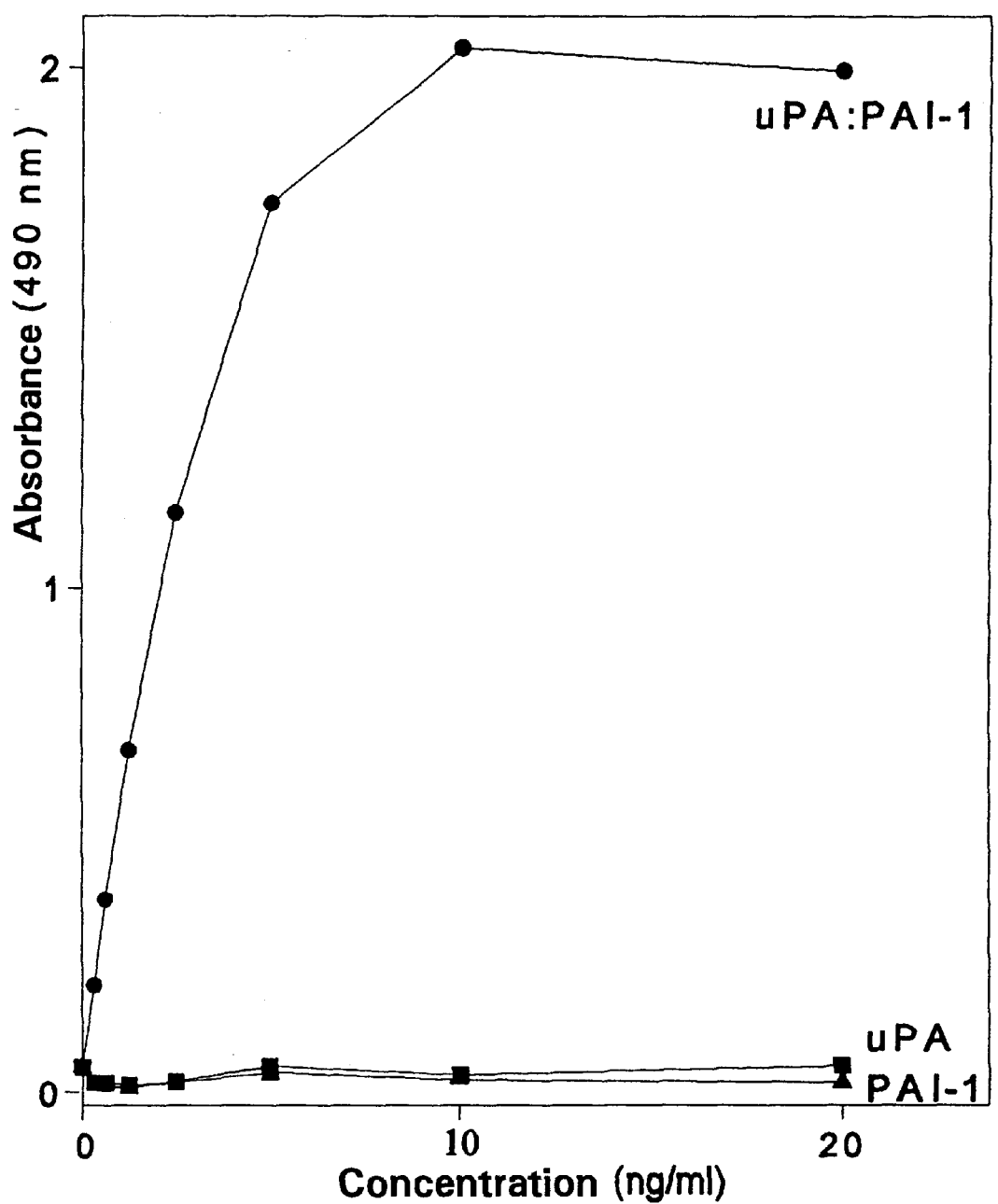
FIG. 9 shows a uPA:PAI-1 complex ELISA measuring uPA:PAI-1 standard (●–●), uPA (■–■) and PAI-1 (▲–▲)

The patients from whom the tumour cytosols were obtained all had surgery for breast cancer. Breast cancer cytosols were prepared according to EORTC guidelines uPA:PAI-1 ELISA uPA:PAI-1 complexes were determined using a sandwich ELISA with a polyclonal uPA antibody as catching antibody and a monoclonal PAI-1 antibody as detecting antibody. A uPA:PAI-1 standard was prepared from HT-1080 sarcoma cell affinity purified PAI-1 activated with 4 M guanidium HCl and incubated with human active uPA (Serono). The sensitivity of the ELISA is 1.5 ng/ml uPA:PAI-1 complexes (FIG. 9). No reactivity was found with pro-uPA, active uPA, latent PAI-1, active PAI-1 or active uPA incubated with latent PAI-1 (FIG. 9).

Results

By measuring with the above-mentioned ELISA, uPA:PAI-1 complexes in breast cancer cytosols obtained from 13 individual breast cancer patients, immunoreactivity could be detected in all samples. Futhermore, large variations among the individual cytosols were observed (FIG. 10).

What is claimed is:

1. A monoclonal antibody which binds a human endothelial type plasminogen activator inhibitor (PAI-1) produced by dexamethasone-treated human HT-1080 fibrosarcoma cells (ATCC (CL121).

2. The antibody of claim 1, wherein said antibody also binds human PAI-1 obtained from human endothelial cells and human platelets.

3. The antibody of claim 2 wherein said antibody binds a complex comprising a urokinase-type plasminogen activator and a human PAI-1 obtainable from dexamethasone-treated human fibrosarcoma HT-1080 cells, and which neutralizes the plasminogen activator inhibitor activity of said human plasminogen activator inhibitor.

4. The antibody of claim 2, which binds specifically to an antigenic determinant of human PAI-1 which is also specifically bound by the monoclonal antibody secreted by the hybridoma of clone 2 (DSM ACC 2489 and ECACC 01010303).

5. The antibody of claim 2, wherein said antibody binds a complex comprising urokinase-type plasminogen activator and a human PAI-1 obtained from dexamethasone-treated human HT-1080 fibrosarcoma cells, and which does not neutralize the plasminogen activator inhibitor activity of said human ePAI.

6. The antibody of claim 5, which binds specifically to an antigenic determinant of human PAI-1 which is also specifically bound by the monoclonal antibody secreted by the hybridoma of clone 4 (ECACC 00112120).

7. The antibody of claim 1, wherein said antibody does not bind a complex comprising urokinase-type plasminogen activator and a human PAI-1 obtainable from dexamethasone-treated HT-1080 human fibrosarcoma cells.

8. The antibody of claim 2, which binds specifically to an antigenic determinant of a human PAI-1 which is also specifically bound by a monoclonal antibody secreted by a hybridoma selected from the group consisting of clones 1 (ECACC 00112117) and 3 (DSM ACC 2490 and ECACC 01010304).

9. The antibody of claim 2, which is not cross-reactive with an endothelial type plasminogen activator inhibitor obtainable from bovine aortic endothelial cells.

10. In a method of producing a monoclonal antibody wherein myeloma cells are fused with antibody-producing mammalian cells, to form a hybridoma cell which produces said monoclonal antibody, the improvement comprising immunizing a mammal with an immunizing agent comprising human PAI-1 obtained from dexamethasone-treated HT 1080 human fibrosarcoma cells, thereby producing the monoclonal antibody of claim 1.

11. The method of claim 10 in which the immunizing agent is depleted of urokinase plasminogen activator produced by said cells.

12. The method of claim 10, wherein the antibody-producing mammalian cells are mouse cells.

13. A method of producing a monoclonal antibody according to claim 1 against human PAI-1 which comprises:
(a) culturing, in a suitable culture medium, dexamethasone-treated HT-1080 human fibrosarcoma cells which are capable of producing a human PAI-1 under conditions conductive to the production and secretion of the PAI-1 into the culture medium;
(b) recovering PAI-1 from the culture medium;
(c) immunizing a mammal with an immunizing agent comprising said recovered PAI-1;
(d) fusing antibody-producing cells from said mammal with myeloma cells to obtain hybridoma cells; and
(e) identifying hybridoma cells which produce a monoclonal antibody against human PAI-1.

14. The method of claim 13 in which the immunizing agent is depleted of urokinase plasminogen activator produced by said cells.

15. The method of claim 13, wherein the antibody-producing cells are mouse cells.

16. The antibody of claim 1 which neutralises the inhibitory effect of the PAI-1 produced by dexamethasone-treated HT-1080 human fibrosarcoma cells (ATCC CCL 221) on activation plasminogen by u-PA.

17. The antibody of claim 2 which neutralises the inhibitory effect of the PAI-1 produced by dexamethasone-treated HT-1080 human fibrosarcoma cells (ATCC CCL 121) on activation of plasminogen by u-PA.

18. An antibody produced by the method of claim 10.

19. An antibody produced by the method of claim 13.

20. The method of claim 10 where said monoclonal antibody is one which neutralises the inhibitory affect of the PAI-1 produced by dexamethasone-treated human HT-1080 fibrosarcoma cells (ATCC CCL 121) on activation of plasminogen by u-PA.

21. The method of claim 13 where said monoclonal antibody is one which neutralises the inhibitory affect of the PAI-1 produced by dexamethasone-treated human HT 1080 fibrosarcoma cells (ATCC CCL 121) on activation of plasminogen by u-PA.

* * * * *